(12) United States Patent
Sauer et al.

(10) Patent No.: US 6,307,674 B1
(45) Date of Patent: Oct. 23, 2001

(54) VIDEO DISPLAY SYSTEM FOR LOCATING A PROJECTED IMAGE ADJACENT A SURGICAL FIELD

(75) Inventors: Jude S Sauer, Pittsford; John F Hammond, Canandaigua, both of NY (US)

(73) Assignee: LaserSurge, Inc., Victor, NY (US)

( * ) Notice: Subject to any disclaimer, the term of this patent is extended or adjusted under 35 U.S.C. 154(b) by 0 days.

(21) Appl. No.: 08/948,803

(22) Filed: Oct. 10, 1997

Related U.S. Application Data

(63) Continuation-in-part of application No. 08/673,612, filed on Jun. 25, 1996, now Pat. No. 6,020,917, which is a continuation-in-part of application No. 08/219,492, filed on Mar. 29, 1994, now Pat. No. 5,543,832.

(51) Int. Cl.$^7$ .......................... G03B 21/56; A61B 19/00; G01N 31/00
(52) U.S. Cl. ................. 359/443; 128/897; 436/1
(58) Field of Search ............... 128/897; 359/443, 359/449; 436/1

(56) References Cited

U.S. PATENT DOCUMENTS

| | | | |
|---|---|---|---|
| 2,625,852 | * | 1/1953 | Van Orden ................ 88/24 |
| 3,682,527 | * | 8/1972 | Pirelli ..................... 359/449 |
| 4,121,714 | * | 10/1978 | Daly et al. ............... 206/363 |
| 4,184,755 | * | 1/1980 | Burgess et al. .......... 353/45 |
| 4,297,001 | * | 10/1981 | Antes et al. ............. 350/129 |
| 4,407,960 | * | 10/1983 | Tratnyek ................. 436/1 |
| 4,557,381 | * | 12/1985 | Whitney .................. 206/440 |
| 5,518,927 | * | 5/1996 | Malchesky et al. ...... 436/1 |
| 5,543,832 | * | 8/1996 | Oravecz et al. ......... 348/65 |
| 5,969,315 | * | 10/1999 | Schulze .................. 235/91 |
| 6,024,094 | * | 2/2000 | Utecht .................... 128/898 |

OTHER PUBLICATIONS

McNamara et al., Fluorophotometry in Contact Lens Research: The Next Step May 1998 Optometry and Vision Science, vol. 75, No. 5.*

Thorat et al., γ–Ray Induced Degradation: A Comparative Study for Homo–and Copolymers of Polypropylene. 1997, Journal of Applied Polymer Science vol. 65, 2715–2720.*

* cited by examiner

*Primary Examiner*—Christopher E. Mahoney
(74) *Attorney, Agent, or Firm*—Brian B. Shaw, Esq.; Stephen B. Salai, Esq.; Harter, Secrest & Emery LLP

(57) ABSTRACT

A method and apparatus for projecting an image of a patient to intersect a display screen which is nonperpendicular to an adjacent portion of an optical path and adjacent a sterile operative field. A video projector system and accompanying optics impart at least one of a tilted focal plane or depth of focus to the projected image. The optical path of the projected image is located adjacent the surgical field. An initially sterile display screen is located in the optical path adjacent the sterile field so that a normal to the screen is noncoincident with the optical path and the projected image on the screen is of constant focus across the screen. The initially sterile display screen may be degradable upon cleaning and resterilization so that a new screen must be used with each procedure, thus insuring the optical quality and sterility of the screen. The display screen may be supported adjacent the surgical field by an articulated rod assembly. The rod assembly may have an upper rod shaped like a "dog leg" for providing easy access by the surgical team for rotating and moving the system up and down. A lower rod of the rod assembly may be connected to the upper rod with a universal joint for adjusting screen location and quickly moving the display screen out of the surgical field.

14 Claims, 23 Drawing Sheets

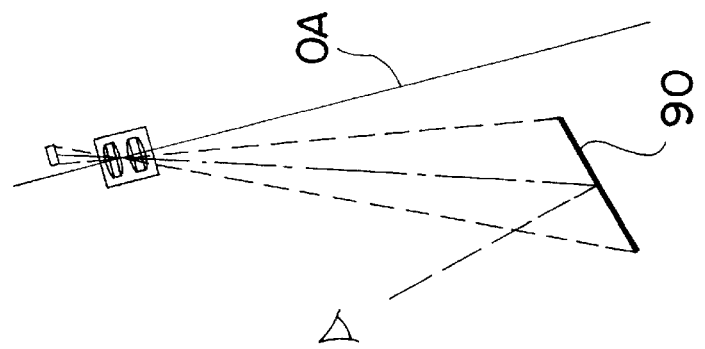
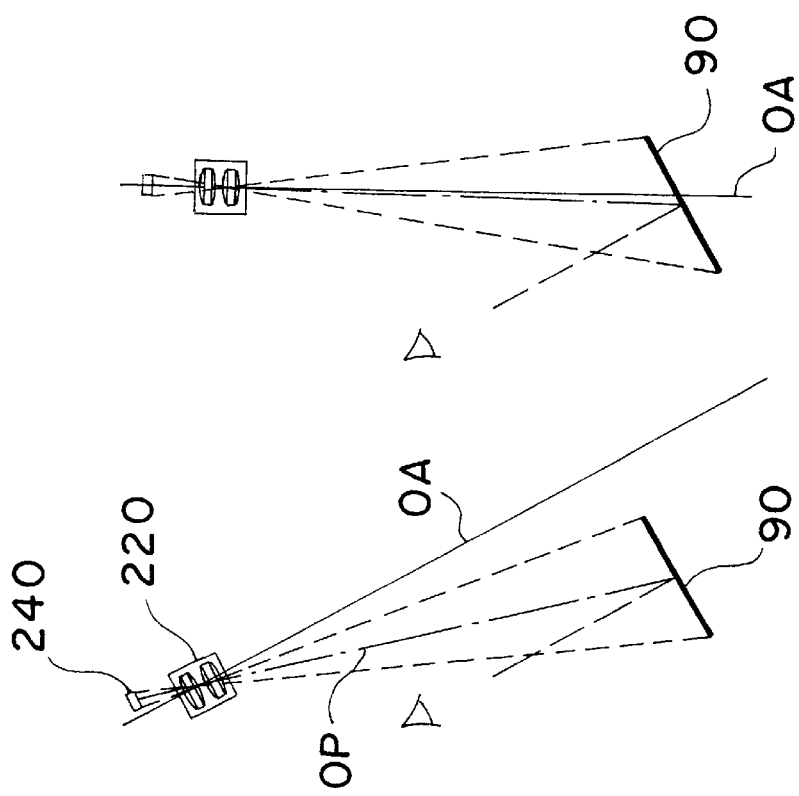
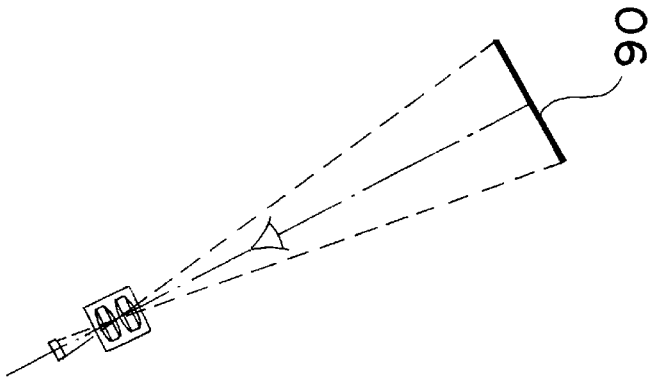
FIG. 12
FIG. 11
FIG. 10
FIG. 9

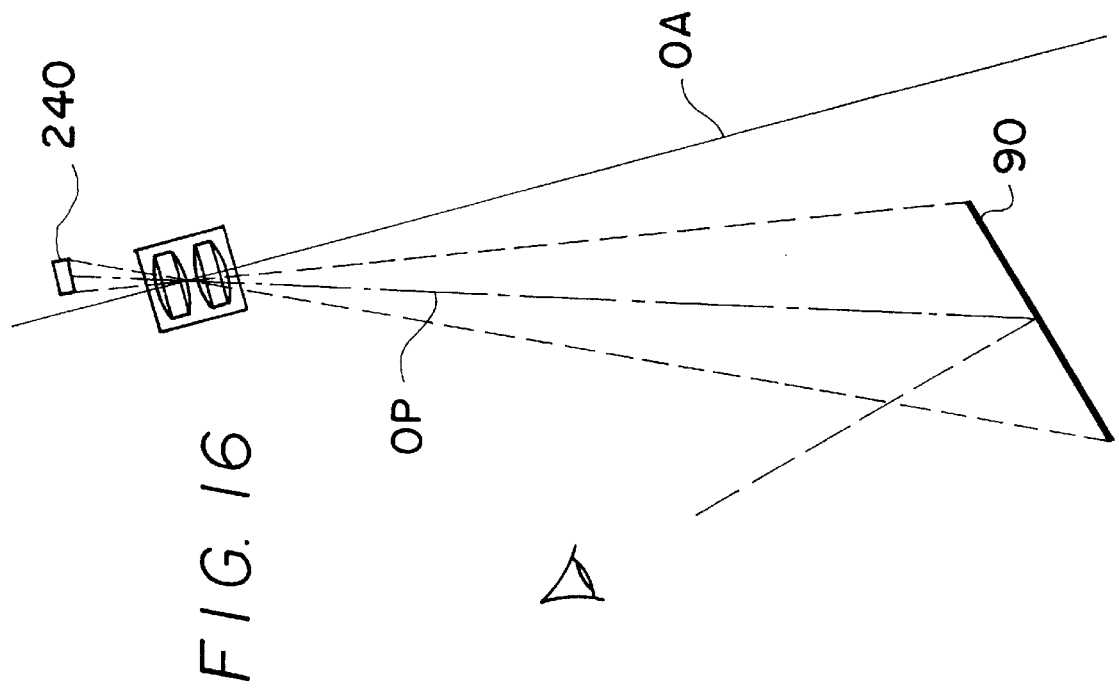
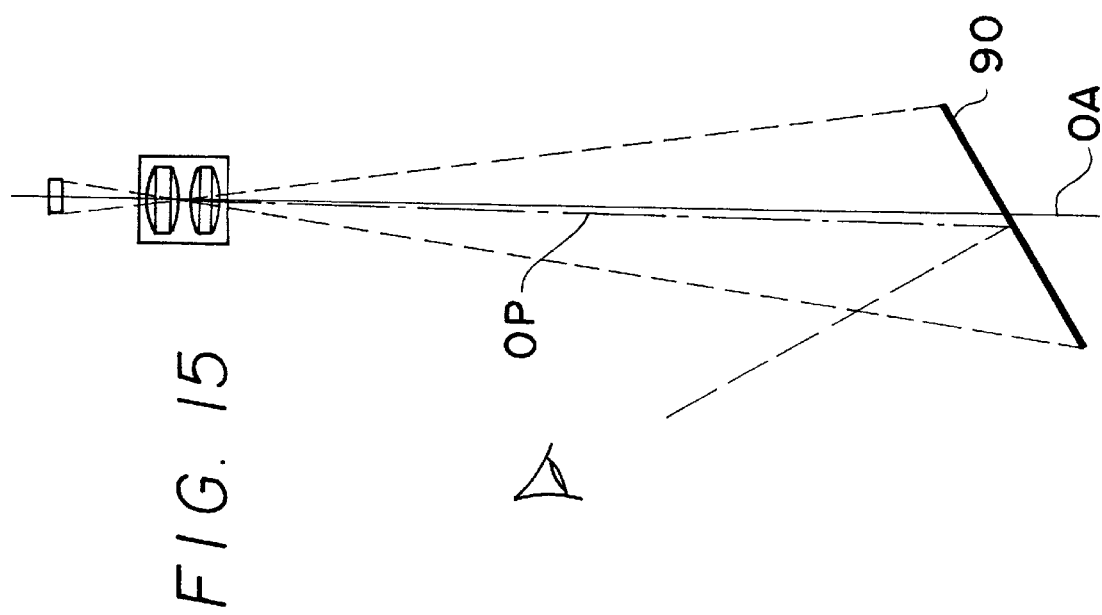

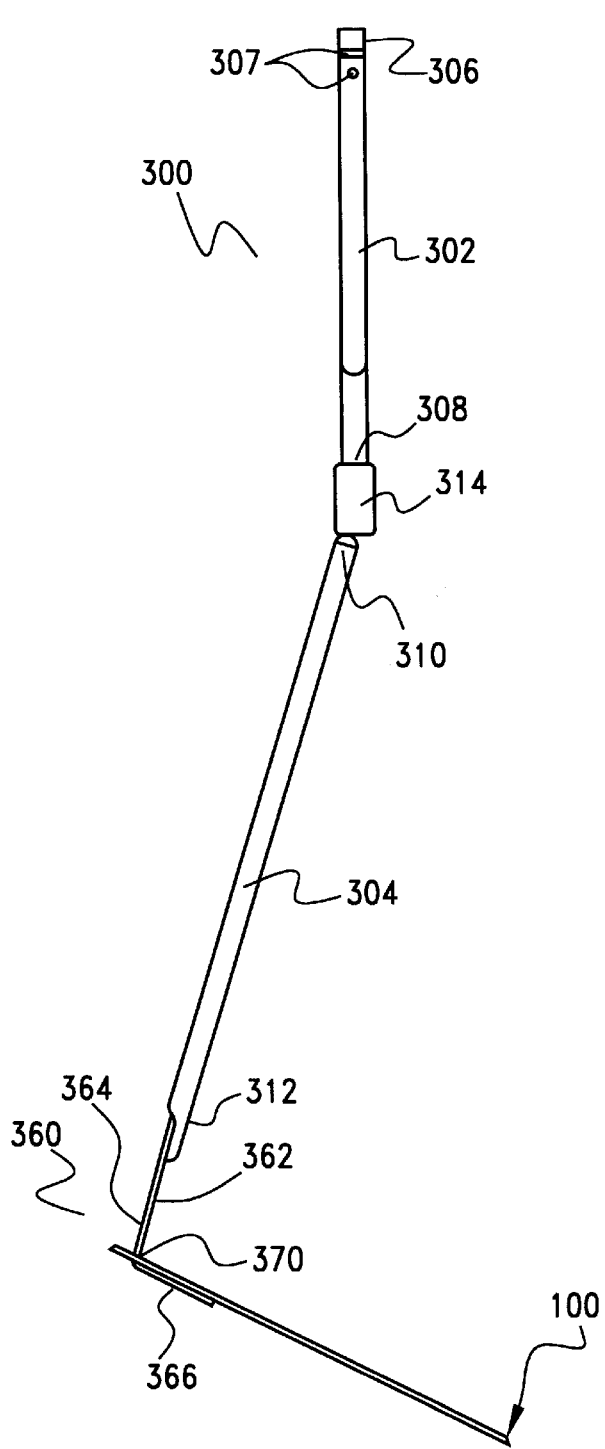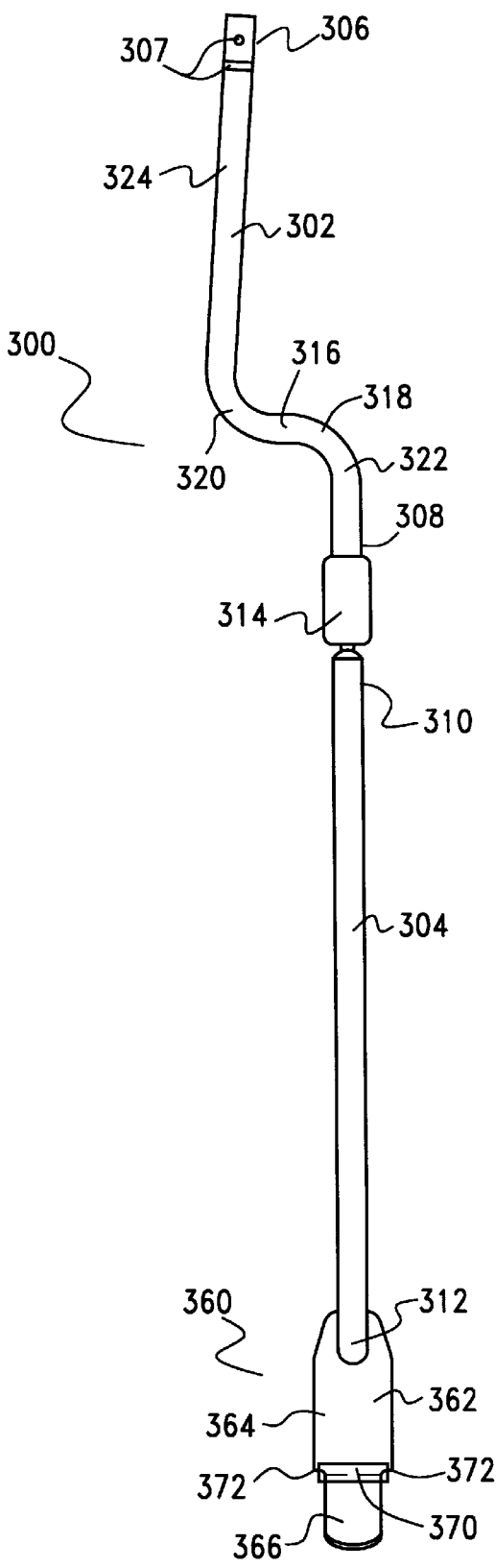
FIG. 21
FIG. 22

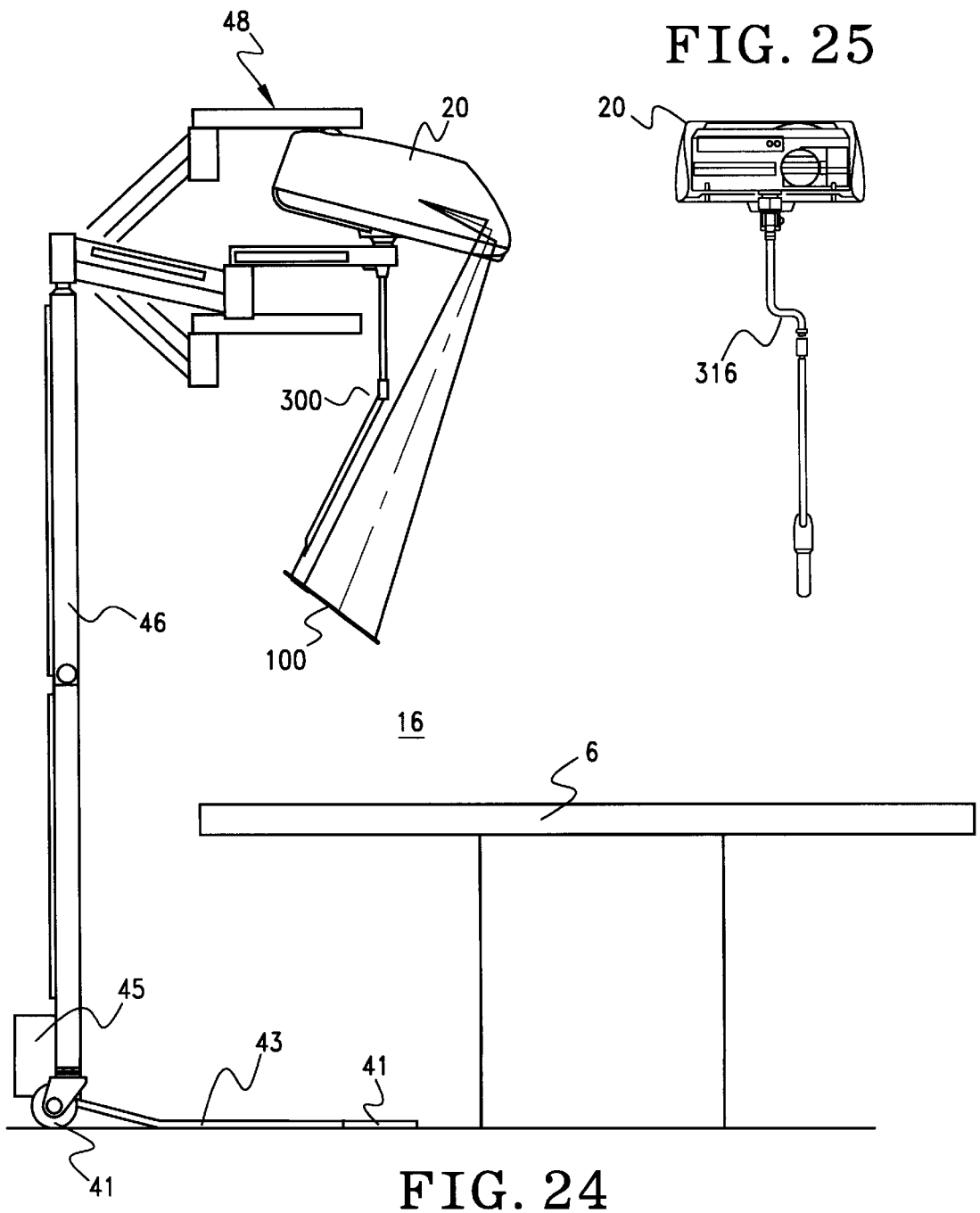

VIDEO DISPLAY SYSTEM FOR LOCATING A PROJECTED IMAGE ADJACENT A SURGICAL FIELD

The present application is a continuation in part of U.S. patent application, Ser. No. 08/673,612 filed Jun. 25, 1996 now U.S. Pat. No. 6,020,917, herein incorporated by reference, which is a continuation in part of U.S. patent application Ser. No. 08/219,492, filed Mar. 29, 1994 now U.S. Pat. No. 5,543,832 naming Michael Oravecz et al., herein incorporated by reference.

FIELD OF THE INVENTION

The present invention relates to video display systems for displaying an image of a patient, and more particularly, to a method and apparatus for projecting a medical image along an optical path and upon a viewing screen adjacent to an aseptic or sterile field. For convenience of disclosure, any medical intervention utilizing sterile techniques will be simply referred to as a surgical procedure.

BACKGROUND OF THE INVENTION

Surgical procedures are often performed in surgical fields which are of a limited size or beneath the skin. With respect to endoscopic procedures, there are several methods for viewing the body interior. For example, the surgeon may look directly through the eyepiece of the endoscope. Alternatively, a beam splitter may be used to provide a second eyepiece for a surgical assistant to simultaneously view the surgical field. For those instances where more than two simultaneous views are necessary, the second view is replaced with a video camera. Splitting the beam between the eyepiece and video camera allows the surgeon to view the surgical field in a high resolution display while the video camera and monitor allow the remaining members of the surgical team to view the procedure. Alternatively, a video camera is mounted directly to the endoscope and one or more monitors are located about the operating environment so that the surgical team may view the field.

Alternatively, liquid crystal display (LCD) monitors can be employed. However, the LCD monitors have a limited viewing angle and an LCD having a sufficient size to permit sufficiently high resolution creates a substantial intrusion to the operating environment. In addition, the LCD monitors are nondisposable, thereby creating a sterilization problem. Further, the accompanying electronics and wires add undesired clutter to the operating environment.

The disadvantages of the prior systems include disorientation created by locating the monitor or projected image of the surgical field remotely from the surgical field. This disorientation is enhanced by the surgeon being unable to view the area of the surgical field and their hands simultaneously. In addition, forcing the surgeon to focus on an image at a relatively large distance while the surgeon's hands are adjacent the body is an unnatural perspective detrimental to the efficiency of surgeons. In addition, constraints on the available locations of the video monitors relative to the surgical field are such that the direction of movement of an instrument within the surgical field is often not translated into a movement in the same direction in the projected image.

Therefore, a need exists for a video display system for an operating environment, wherein a high resolution projected image of a surgical field or other video information may be located adjacent the surgical field or in a viewing orientation which is optimal to the surgeon. In addition, the need exists for a video display system which presents an image which is consistent with the direction of movement within the surgical field. The need also exists for a sterile disposable screen that can sustain permitting contact with the surgical team, or blood and other bodily fluids during the surgical procedure. The need further exists for a single-use sterile viewing screen which precludes resterilization by degrading. Thus, the display screen will degrade to an inoperative configuration upon washing and resterilization. As a new sterile display screen must be used for each procedure, sterility and optical quality are ensured. The need also exists for a viewing screen which may be located at a favorable viewing angle without jeopardizing the integrity of the projected image. A need further exists for a projector and display screen which are physically linked so that a reorientation of the screen causes a corresponding reorientation of the projector to maintain the integrity of the displayed image. A need further exists for a screen support which enables the screen to be easily and quickly repositioned within the surgical field and which enables the surgical team to easily grasp and move the system without comprising their sterile status. A need further exists for a simple screen mounting system which can mount a viewing screen in a stable orientation.

SUMMARY OF THE INVENTION

Thus, it is an object of the present invention to provide a sterile single use projection screen for a medical imaging system that degrades if resterilization is attempted. It is a further object to provide a sterile single use projection screen for a medical imaging system wherein the sterile screen comprises a layer of reflective material for forming an image by reflection from a projector. A further object includes a sterile single use projection screen for a medical imaging system, wherein the sterile screen further comprises a layer of degradable material bonded to a layer of reflective material for maintaining the layer of reflective material in a substantially flat condition for imaging, and degrading to prevent formation of a usable image if the screen is resterilized.

Yet another object includes a sterile single use projection screen for a medical imaging system having a slot adjacent one edge of the layer of reflective material, for receiving a support for the screen. Another object includes a sterile single use projection screen for a medical imaging system having a recess in the layer of degradable material for receiving a folded sleeve. The present invention also has the object of a sterile single use projection screen for a medical imaging system having a sticker overlapping the recess, having a layer of adhesive in the area overlying the degradable layer, and being substantially free from adhesive in the portion overlying the recess. Another object includes a sterile single use projection screen for a medical imaging system having a slot adjacent one edge of the layer of degradable material, aligned with the slot in the layer of reflective material, for receiving a support for the screen. Another object includes a sterile single use projection screen for a medical imaging system in which the degradable layer comprises a layer of paper. A further object is a sterile single use projection screen for a medical imaging system in which the layer of reflective material comprises a layer of plastic.

The present invention includes a video projection system designed for a sterile operating environment for locating a viewing screen at an optimum viewing angle adjacent a surgical field and within the reach of the viewers. As the screen is adjacent the surgical field and within reach of the surgical field, direct eye and hand coordination is enhanced as viewers can simultaneously view the display of the surgical field and their hands. In addition, communication is facilitated by permitting manual referencing to the images on the view screen to unequivocally identify areas within the surgical field. Locating the projected image adjacent the surgical field also reduces fatigue of the surgeons.

In an embodiment of the invention, an endoscopic surgical field is displayed upon a viewing screen adjacent the surgical field. A high resolution small screen projection system projects the endoscopic image along an optical path. The projected image may be characterized by a focal plane that is non perpendicular to the optical path. Mirrors locate the optical path adjacent the surgical field. A sterile single use, disposable viewing screen is retained along the optical path adjacent the surgical field at a predetermined distance from the projector at a nonperpendicular angle to the optical path. The projection optics and angle between the optical path and the normal to the screen provides uniform focus of the entire projected image upon the screen.

In an embodiment of the invention, a projected image is created to exhibit a depth of focus extending along the optical path. The viewing screen may then be disposed in the optical path with a normal to the screen being nonperpendicular angle to the optical path such that the projected image is of substantially uniform focus across the viewing screen. In a further embodiment, the focal plane is non perpendicular to the optical path by the application of tilted or decentered projection optics.

In an embodiment of the invention, the projector and the display screen are connected in a fixable relationship, and this relationship can be reoriented with respect to a support stand. That is, the projector and display screen are set in a given relative position to each other and the projector and the display screen may be moved together as a unit relative the a support stand so that the display screen can be relocated with respect to the surgical field without requiring a readjustment or repositioning of the display screen relative to the projector.

The foregoing and other features and advantages of the invention will be more readily understood and fully appreciated from the following detailed description, taken in conjunction with the accompanying drawings.

BRIEF DESCRIPTION OF THE DRAWINGS

FIG. 9 is a side elevation view of standard projection optics;

FIG. 10 is a side elevation view of decentered projected optics;

FIG. 11 is a side elevational view of tilted projection optics;

FIG. 12 is a side elevational view of tilted and decentered projection optics;

FIG. 15 is an enlarged side elevational view of tilted projection optics;

FIG. 16 is an enlarged side elevational view of tilted and decentered projection optics;

FIG. 21 is a side elevational view of a rod assembly, screen mounting assembly and viewing screen;

FIG. 22 is a front elevational view of the rod assembly, screen mounting assembly, and viewing screen of FIG. 21;

FIG. 24 is side elevational view of the second embodiment of the present invention used with a mobile stand and adjacent a surgical table;

FIG. 25 is a front elevational view of portions from FIG. 24;

DETAILED DESCRIPTION OF THE PREFERRED EMBODIMENTS

Figure 1:
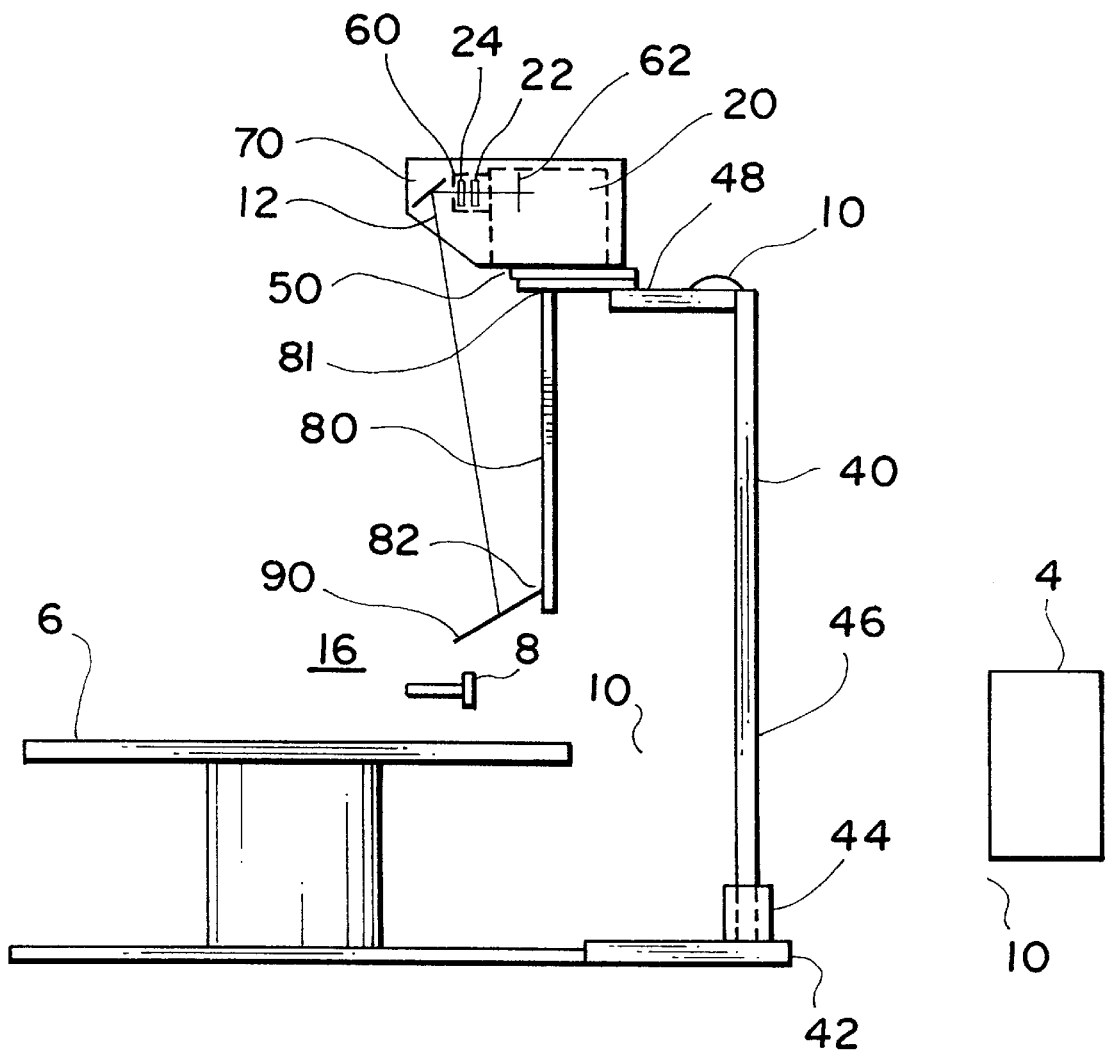
FIG. 1 is a side elevational view of a first embodiment of the present invention.
Figure 2:
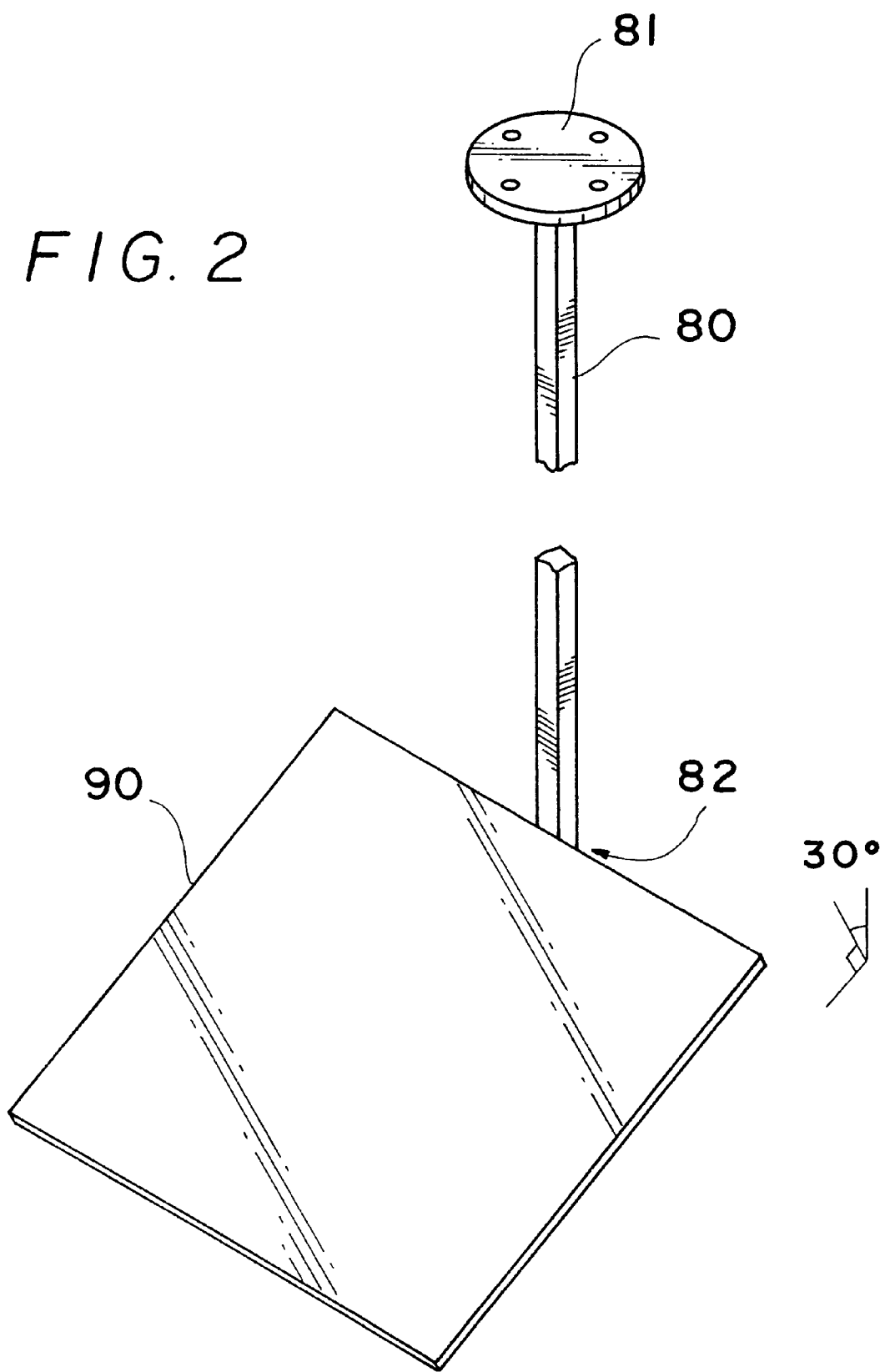
FIG. 2 is a broken perspective view of the viewing screen.
Figure 17A:
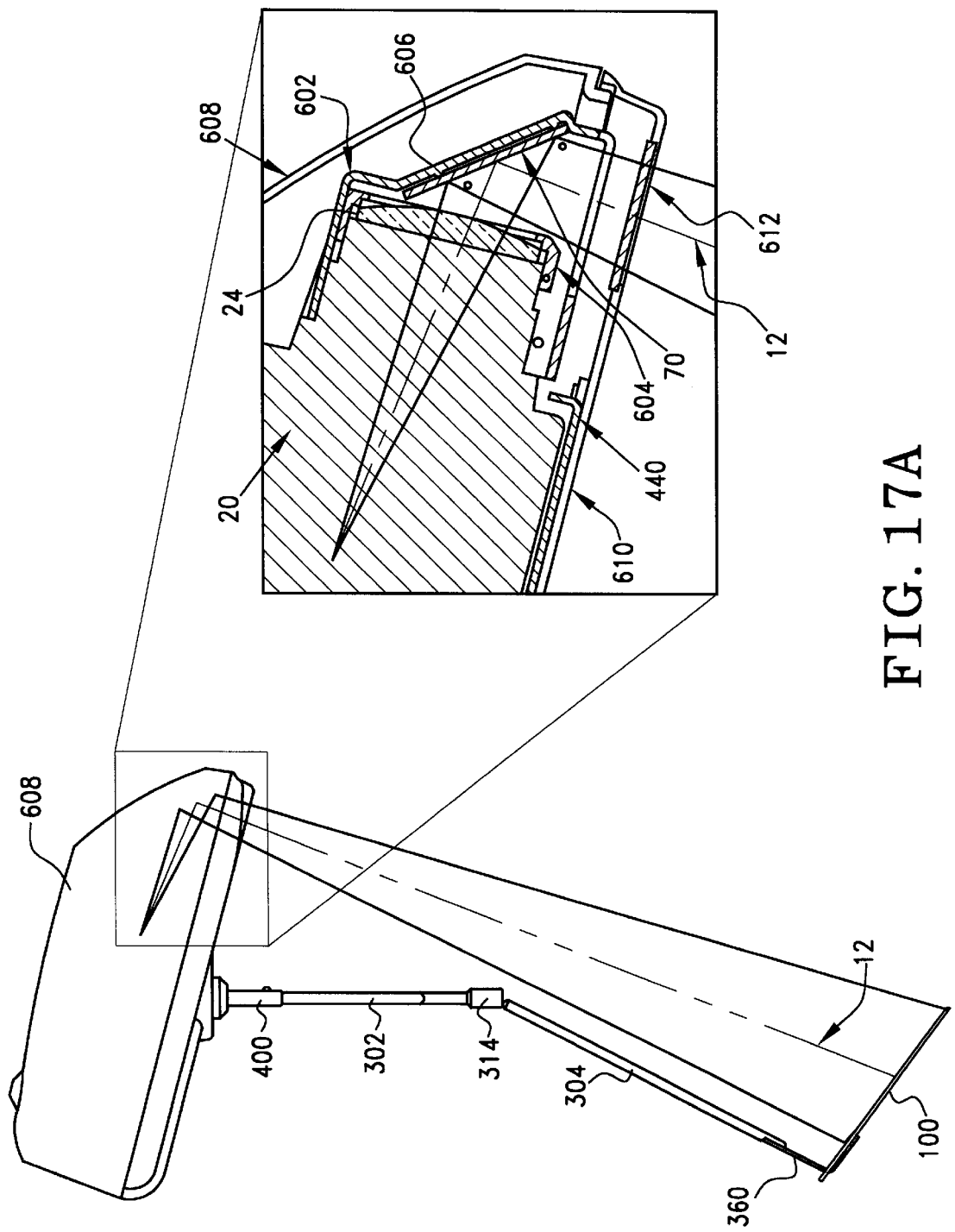
FIG. 17A is a side elevational view of a third embodiment of the present invention.

Referring to FIG. 1, a first embodiment of the present invention is disclosed. A video projector 20 is supported by a stand 40 to be remotely located from an operating table 6 and surgical field 16. The video projector 20 projects an image along an optical path 12, wherein the optical path passes through a projection optic 60 and intersects a sterile display screen 90. The screen 90 may also be termed a viewing screen. When used in combination with the projector 20, the screen may be termed a projection screen. As shown in FIGS. 17A, 21, and 24, a viewing screen 100 is mounted to a screen mount assembly, which in turn is connected to a screen rod assembly 300. An image gathering system 8, such as an endoscope, as well known in the art is used to gather the image to be projected by the projector 20. The image gathering system 8 is operably connected to the projector 20 via an image gathering system electronic converter 4, as known in the art by a standard transmission line 10, such as a video cable.

The video projector 20 is a self-contained system which projects a high quality, high resolution video image along the optical path 12. Preferably, the projector 20 has a resolution which is substantially equal to a surgical video monitor. The projected resolution is approximately 450×245 pixels (horizontal by vertical). It is understood the resolution of the projector may be higher, or lower. The video projector 20 may be any of a commercial available types such as the L3800 manufactured by Eiki.

In one embodiment, the projection optic 60 includes focusing, zoom optics 22 of the video projector 20 and a diopter lens 24. The diopter lens 24 is any of a variety well known in the art, such as the Professional Ser. 9 Plus ½ lens manufactured by Tiffen. The diopter lens 24 is used to change the focusing range of the focusing, zoom optics 22 of the projector 20 to the nearer distances. The focusing, zoom optics 22 are adjusted to produce an image the size of the viewing screen at a practical projection length. The focusing, zoom optics 22 are also adjusted to focus the image onto the viewing screen.

The projection length along the optical path 12 is sufficiently long to position the projector 20 well above or removed from the operating table 6 and out of the way of personnel and equipment. Preferably, the projection optic 60 and projector 20 location are selected to provide an optimum image size at the point the optical path 12 is adjacent the surgical field 16. For example in general surgery, these selections would provide a projected image that is approximately life size.

As shown in FIG. 1, a mirror 70 directs the optical path 12 from the projection optic 60 downward to viewing screen 90. Although only one mirror 70 is shown, a series of mirrors may be used to locate the optical path 12 relative to the surgical field 16.

Mirror Mount

Figure 17B:
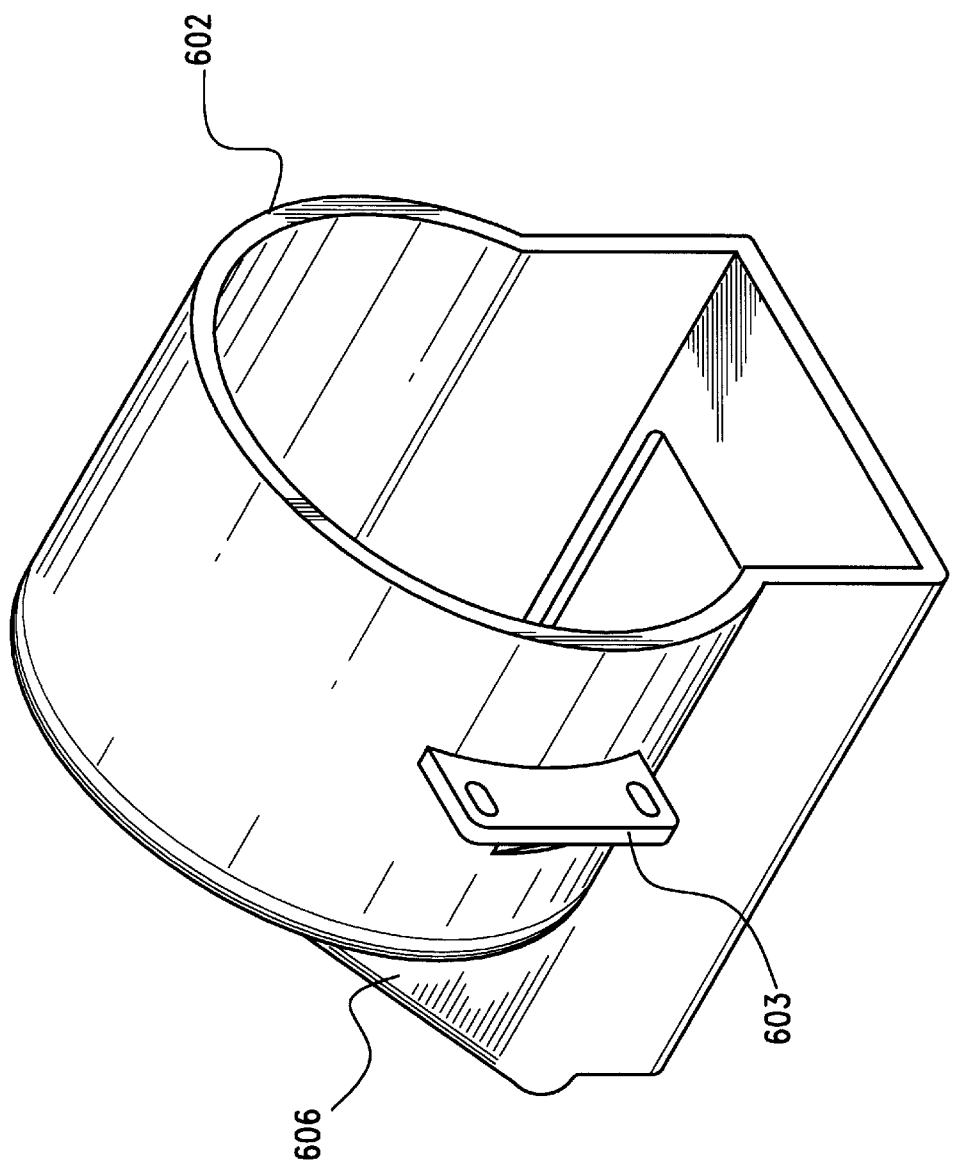
FIG. 17B is a perspective view of a mirror housing in a preferred embodiment of the present invention.

Alternatively, as shown in FIGS. 17A–17B, an embodiment for mounting a reflector or mirror 70 to the projector 20 is shown. The diopter lens 24 is shown adjacent the projector 20 and held in place via a lens mount 604. Surrounding the diopter lens 24, lens mount 604, and any other lenses which may be installed adjacent the projector 20 is a mirror mount 602. The mirror mount is preferably mounted to a zoom ring of a projector 20. The mirror mount 602 includes an angled plane 606 designed to hold a mirror 70 at the appropriate angle to redirect the optical path, the center of the optical path being shown at 12. The mirror mount 602 further includes an adjustment mechanism 603 for locating the mirror 70 along the optical path. The mirror mount includes a retainer for grasping a portion of the projector to prevent unintended separation of the mirror mount and the projector.

Referring to FIGS. 17A and 24, the projector 20, optical components, and the mirror mount are protected from damage and debris by a top cover 608 and bottom cover 610. An optical window 612 may be provided for passing the optical path 12 past the bottom cover 610.

The present system thus allows a surgeon to view a planar viewing display screen upon which an image is remotely projected, wherein the optical path is not intersected by the surgeon.

Figure 5:
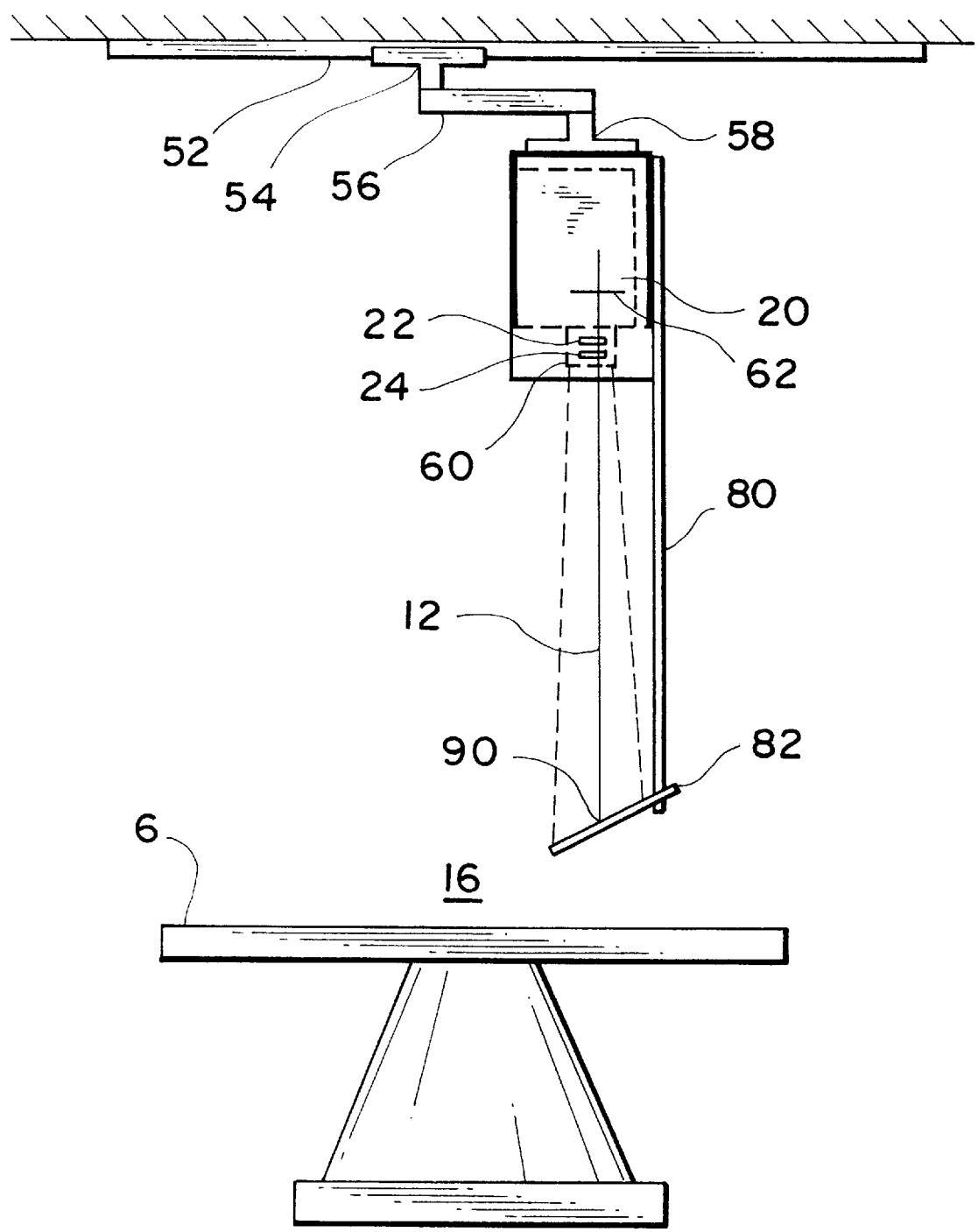
FIG. 5 is a side elevational view of a second embodiment of the invention.
Figure 6:
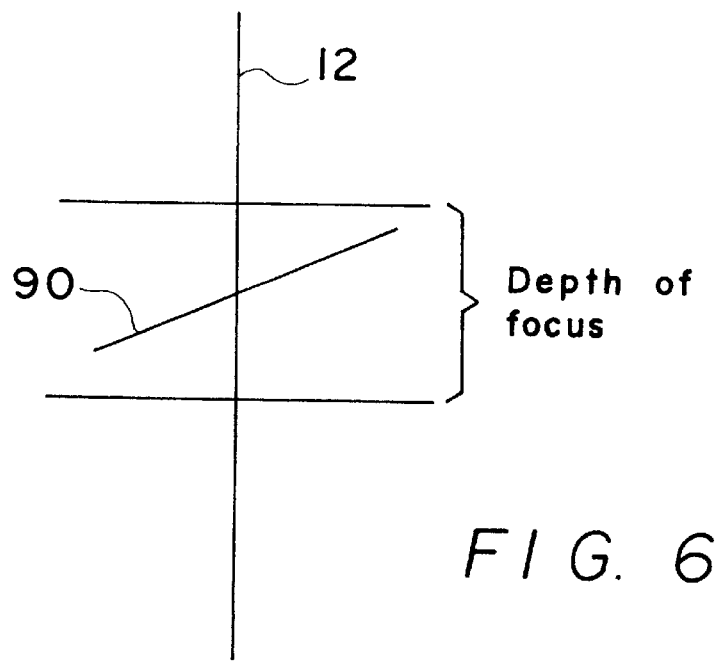
FIG. 6 is a schematic view showing a depth of focus along the optical path.
Figure 7:
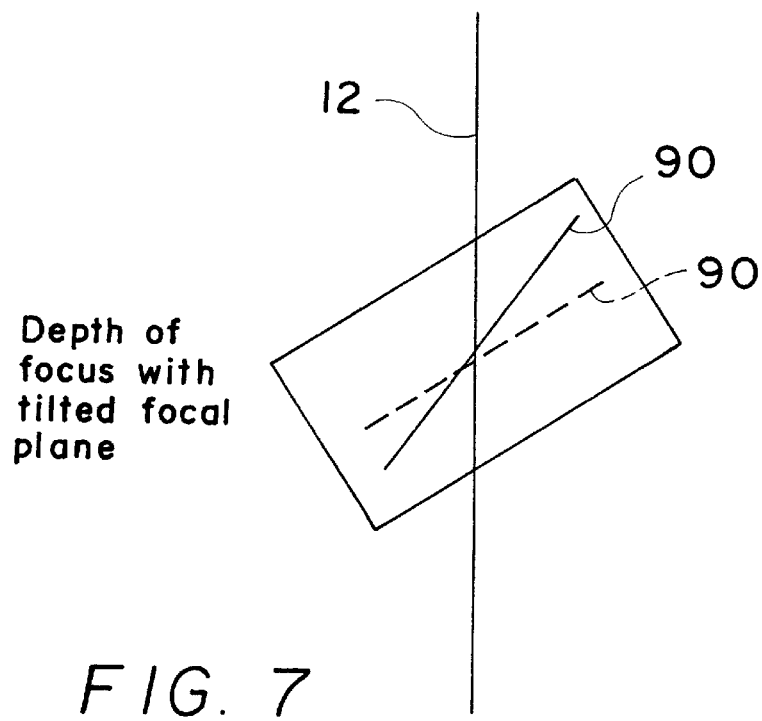
FIG. 7 is a schematic view showing a viewing screen having a normal noncoincident to the adjacent optical path disposed within the projected depth of focus along the optical path.
Figure 8:
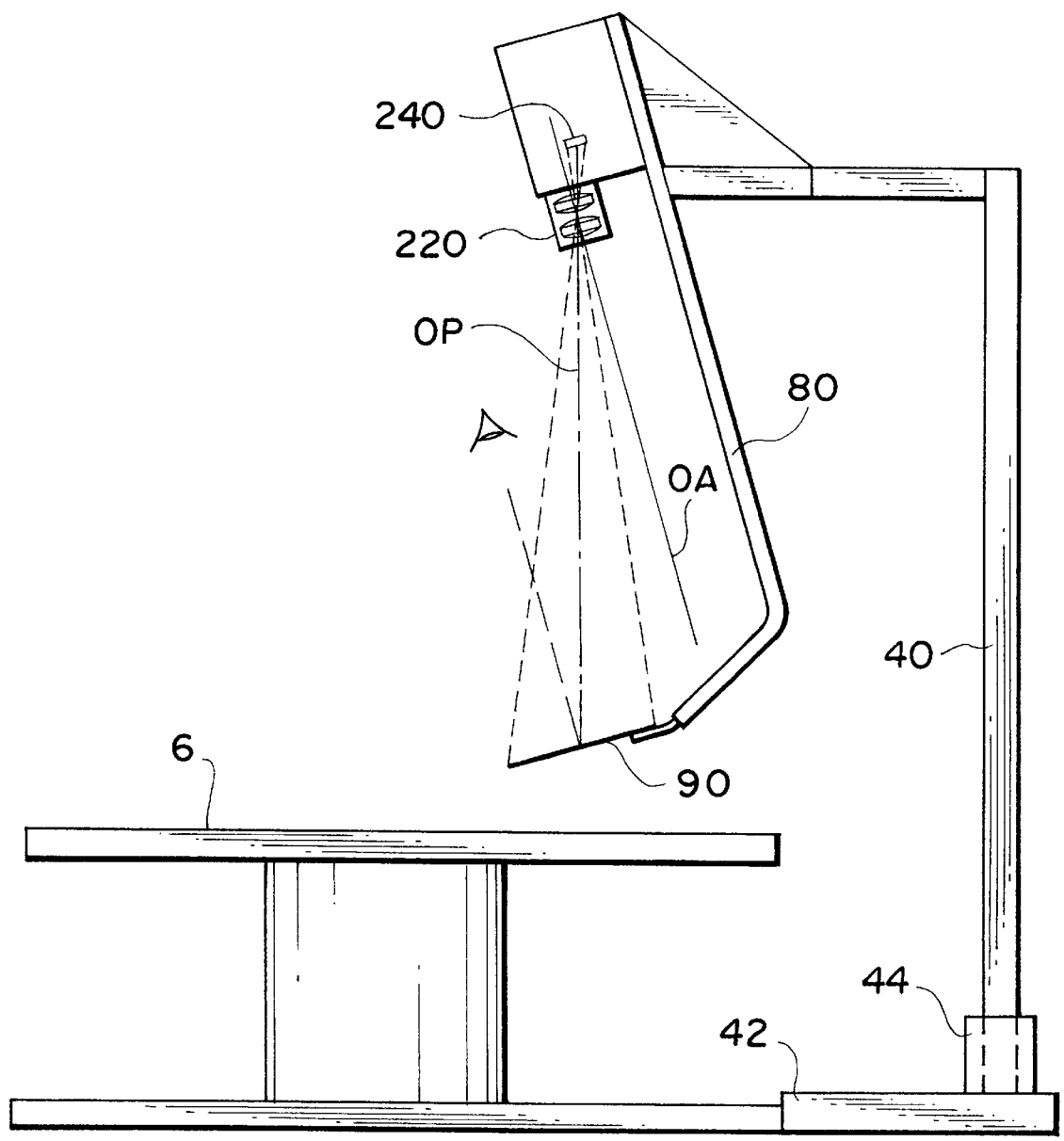
FIG. 8 is a side elevation view of an embodiment showing decentered projection optics.
Figure 14:
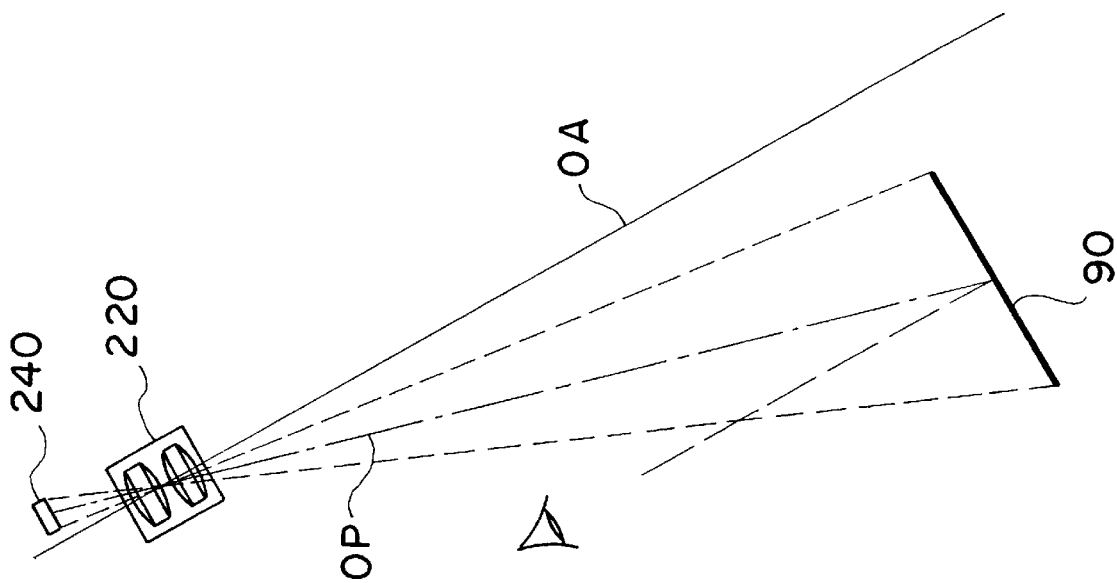
FIG. 14 is an enlarged side elevation view of decentered projected optics.
Figure 13:
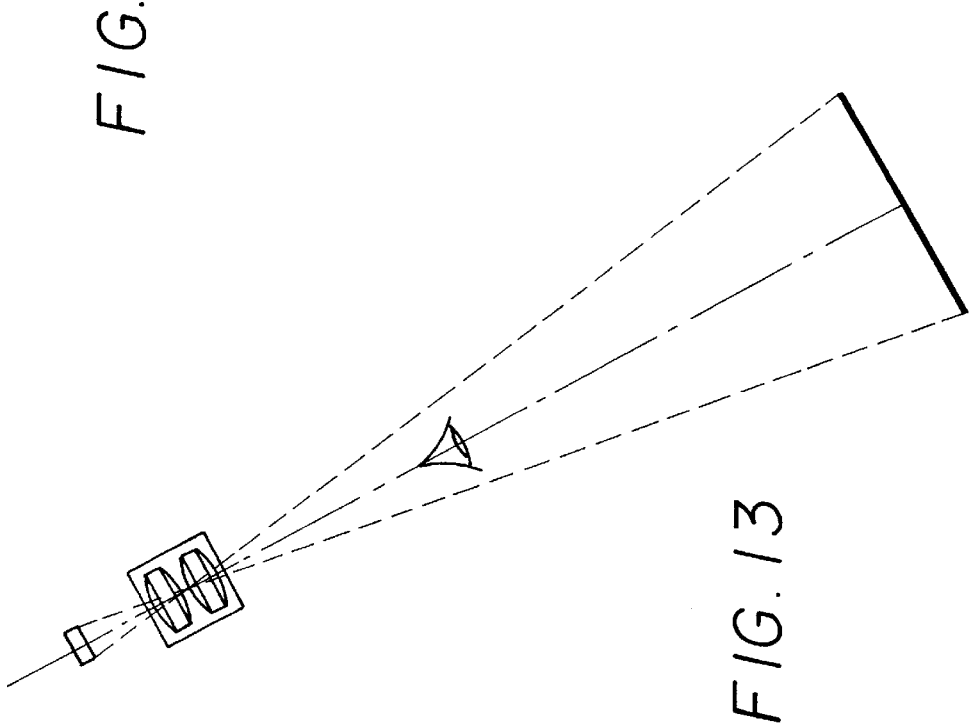
FIG. 13 is an enlarged side elevation view of standard projection optics.

To minimize interference in the operating room and reduce interruption of the projected image, the optical path 12 adjacent the surgical field 16 is substantially vertical and does not include a substantial horizontal component which would interfere with a larger portion of the operating field. Therefore, the foot print of the optical path 12 is substantially minimized. In the embodiments of FIGS. 1 and 5, the adjacent portion of the optical path lies within the foot print of the viewing screen. That is, the viewing screen overlies a certain horizontal area and the adjacent portion of the optical path is within the vertical projection of the horizontal area.

Support Stand

In a preferred embodiment, the stand 40 includes a base 42 and a post 46 extending from the base. As shown in FIG. 24, the base 42 may optimally be wheeled or provided with rollers 41 and further preferably includes low profile legs 43 which can slide underneath an operating table, thus limiting interference with movement about the table.

In a construction of the low profile legs, a substantial length, more than 50 percent, is below an axis of rotation of the wheels. The base includes a wheel strut for operably retaining a pair of spaced apart rollers. At least one and preferably at least two non wheeled floor contacting legs extend downward from the strut to terminate at a spaced location from the strut. The floor contacting legs include a substantial length that contacts the floor. Thus, at least half the length of the floor contacting legs has a height that is defined by the thickness (height) of the legs themselves. The length of contact with the floor is sufficient to require a pivoting of the entire assembly about the strut to provide only rolling contact with the floor.

Preferably, the post 46 extends upward to terminate a distance above the operating table 6. An arm 48 is connected to the post 46 to horizontally locate the video projector 20. The arm 48 may be articulated to allow horizontal adjustment of the arm relative to the base 42. In addition, an isolation transformer 45 is preferably located at the rear of a post 46. Because the transformer 45 is of substantial mass, it can provide counterweight to assist in balancing the stand which must hold the weight of the projector 20 and screen holder system on an upper and opposite side of the stand. Power and video cables 10 may extend within the post 46 and the arm 48 to the projector 20.

Figure 18:
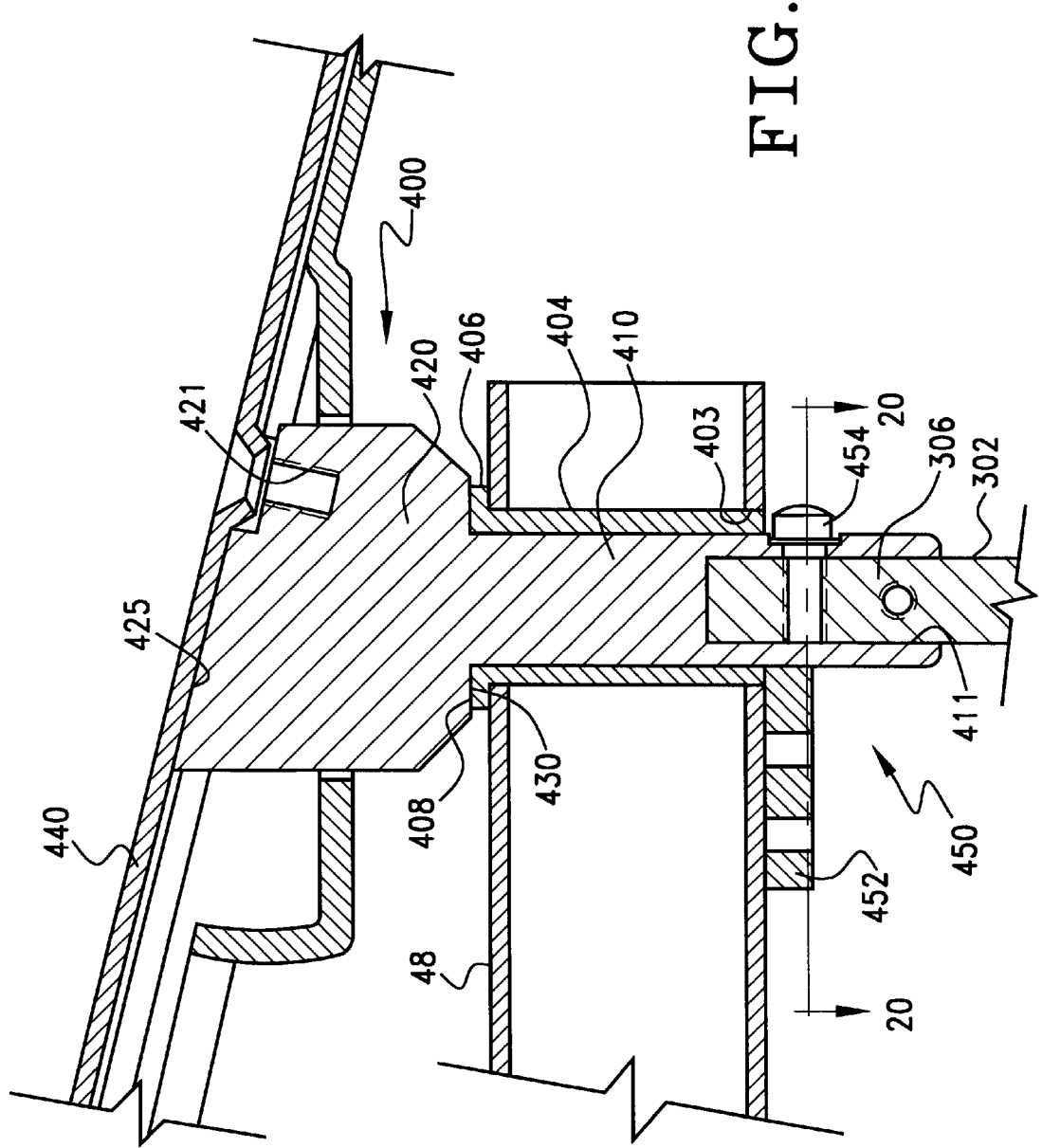
FIG. 18 is a cross-sectional view of a coupler taken along lines 18—18 from FIG. 19.
Figure 19:
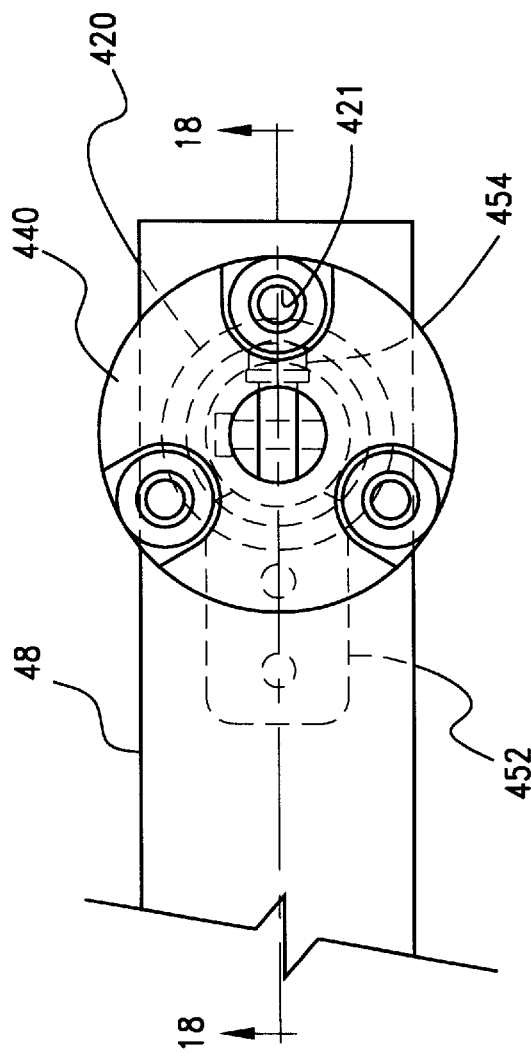
FIG. 19 is a cross-sectional view of FIG. 18.
Figure 20:
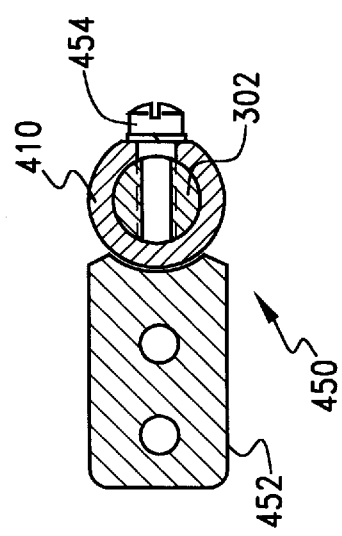
FIG. 20 is a cross-sectional view taken along line 20—20 from FIG. 18.

As shown in FIGS. 18–20, the stand 40 includes a coupler 400 for operably linking the projector 20 and the viewing screen 100 for rotation relative to the stand. The viewing screen 100 is mounted to the screen mount assembly which in turn is connected to the screen rod assembly 300, as will be further described. The screen rod assembly 300 is then connected to the coupler 400 for rotational movement relative to the stand 40. The viewing screen 100 and the projector 20 are thus connected such that rotation of one of the display screen and the projector 20 causes a corresponding rotation of the remaining one of the viewing screen and the projector.

The arm 48 includes an aperture 403. A bearing 404 is retained in the aperture 403. The bearing 404 includes an upper collar 406 sized to preclude passage through the aperture 403. The upper collar 406 defines a contact ring 408.

The coupler 400 is sized to engage the bearing 404. The coupler 400 includes a shaft 410 and a head 420 that define a shoulder 430 therebetween. The shoulder 430 is sized to engage the contact ring 408. The shaft 410 is sized to be retained within the bearing 404. A lower end of the shaft 404 includes a recess 411 for connecting to a proximal end 306 of a first upper rod 302 of the screen rod assembly 300. The head 420 includes at least one and preferably a plurality of mounting recesses 421.

Although it is feasible to mount the projector along a horizontal plane parallel with the floor and operating table 6, as shown in FIG. 1, combining a non horizontal oriented projector with offset optics further facilitates increased viewing screen angulation, as shown in FIG. 24. In this embodiment, an angle of approximately 36° between the viewing screen 100 and the operating table 6 has been found to be well suited for viewing surgical procedures on a viewing screen adjacent a surgical site. To project an image onto a viewing screen 100 at this angle, the projector 20 is preferably mounted at an angle of approximately 14° to compensate for the steeper viewing angle of the display screen 100. The head 420 of the coupler 400 thus includes an angled top surface 425 for setting the angle of the projector.

In addition, the video display system of the preferred invention further includes a rod assembly, for supporting the viewing screen, which is adjustable, as will be further described below.

A mounting plate 440 is connected to the head 420 of the coupler 400 and particularly to the top surface 425. The mounting plate 440 is configured to engage and retain the particular projector 20. Thus, by means of the mounting plate 440 a variety of different projectors 20 can be employed in connection with the present system. The mounting plate 440 allows for connection of the projector by threaded fasteners, cams, locks or friction fits as dictated by the intended orientation of the projector 20 and the stand 40. The coupler 400 provides for operable retention of the projector 20 at an inclined projecting angle.

In addition, a rotation stop 450 may be employed to limit or set a particular orientation of the projector 20 and the display screen 90 with respect to the stand 40. The rotation stop 450 includes a stop plate 452 connected to the arm 48 adjacent the coupler 400 and a corresponding stop screw 454 passing through the coupler and the screen rod assembly. The stop screw 454 may be adjusted to set or limit the rotation of the projector 20 and display screen 90 relative to the stand 40. However, the rotation stop 450 may include an alternative structure for selectively precluding rotation of the coupler 400 with respect to the arm 48 such as pins, cams or lever locks.

In an alternative construction, the coupler 400 may be configured as or cooperate with a universal joint. The use of a universal connection between the projector/screen rod assembly and the stand 40 permits the display screen 90 to be relocated by movement about any of three mutually perpendicular axes. That is, the display screen may change its relative angle of inclination and elevation with respect to the surgical field without compromising the integrity of the image on the viewing screen 100. The universal joint could include a ball and socket type joint for permitting rotation about three mutually perpendicular axes.

The present system thus allows a surgeon to view a planar display or viewing screen upon which an image is remotely projected, wherein the optical path is not intersected by the surgeon.

Alternatively as shown in FIG. 5, the projector 20 may be mounted by a linear track 52 affixed to the ceiling, wherein the track retains an arm mount 54. A counter balanced arm 56 extends from the arm mount 54 to horizontally displace the projector 20. A projector support 58 is connected to the arm mount 54 to operably retain the video projector 20 in a vertically projecting orientation. The coupler 400 is mounted to the projector support 58 to link the projector 20 and the screen rod assembly 300.

Screen Holder

Referring to FIG. 1, in a first configuration, a screen rod 80 depends from the projector base plate 50 and terminates adjacent the operating table 6 and surgical field 16. The screen 90 is affixed to the rod 80 to be located at a predetermined distance from the projector 20. As the rod 80 is mounted upon the articulated arm 48, horizontal location of the screen 90 may be adjusted by bending the joint in the middle of the arm 48 and its junction with the post 46. The rod 80 is rigidly affixed relative to the projector 20 by threaded fasteners, as well known in the art.

Figure 23:
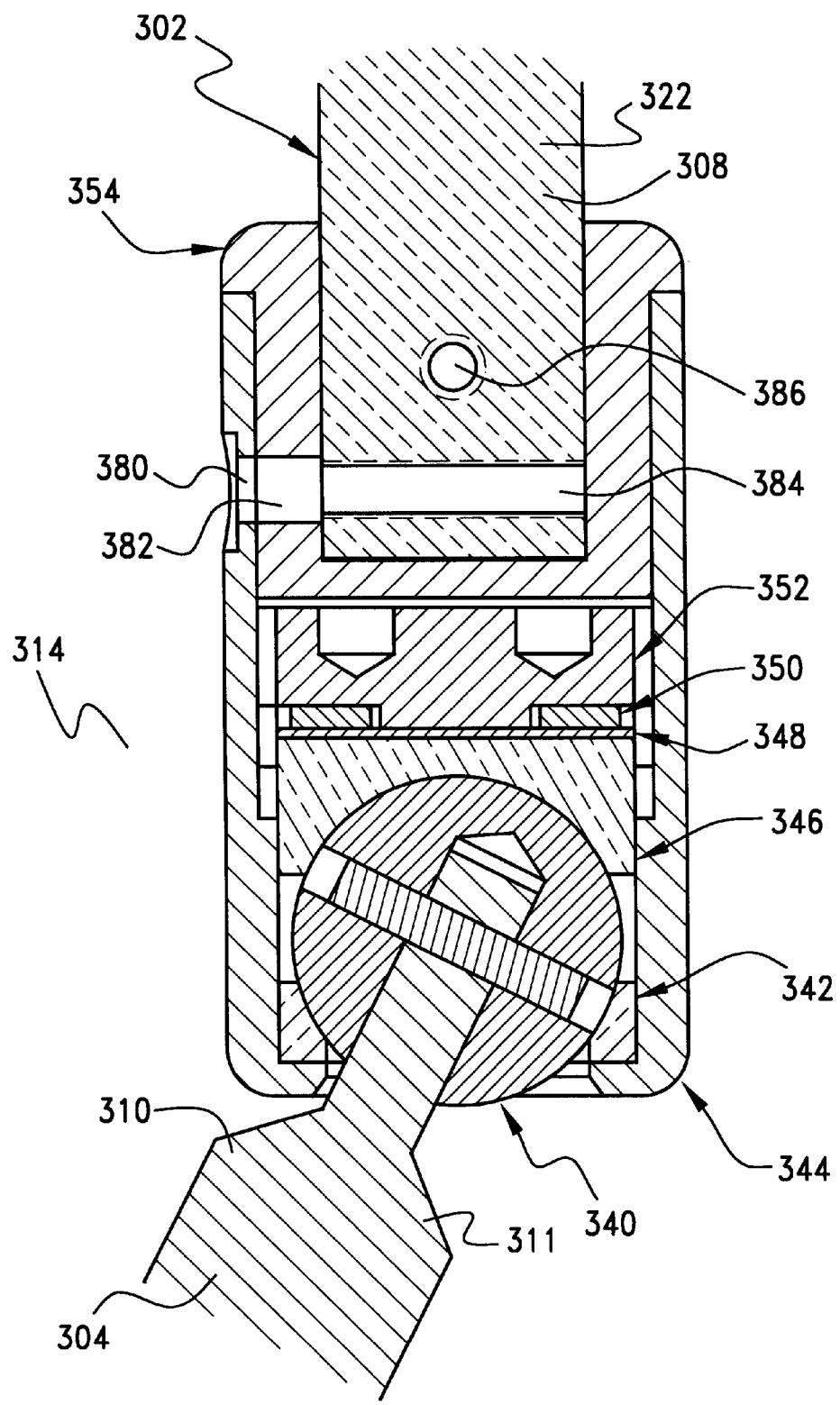
FIG. 23 is a cross-sectional view of a universal joint assembly.

In the embodiment, as shown in FIGS. 21–23, a rod assembly 300 is provided for connecting a viewing screen 100 to the coupler 400 as previously described. For maximum performance, the rod assembly 300 is preferably made from solid stainless steel with nylon or Teflon bearings. The rod assembly 300 preferably comprises an upper rod 302 movably linked to a lower rod 304. The upper rod 302 has a proximal end 306 and a distal end 308. The proximal end 306 is provided with holes 307 for receiving a retention pin and rotation stop screw in the coupler 400. The lower rod 304 has a proximal end 310 and a distal end 312. The distal end 308 of the upper rod 302 is attached to a universal joint assembly 314. The universal joint assembly 314 is attached to the proximal end 310 of the lower rod 304. The distal end 312 may include a cut-away region for receiving a screen mounting assembly as will be described.

The upper rod 302 includes a non collinear section so as to form an integral handle for rotation or vertical adjustment of the projector 20 and viewing screen 100. In one embodiment, the upper rod 302 is preferably in the shape of a "dog leg" rod, otherwise termed as a sigmoid shape. That is, the upper rod 302 is preferably made from a first rod section 324 extending from the proximal end of the rod 302, a second rod section 316 extending away from the rod section 324, and a third rod section 322 extending towards the distal end 308 of the rod 302 and away from the second rod section 316. Thus, the first rod section 324 and third rod section 322 are non-collinear. The first rod section 324 and the second rod section 316 are preferably connected by a rounded elbow 320, and the second rod section 316 and the third rod section 322 are preferably connected by a rounded elbow 318. The first rod section 324 and third rod section 322 preferably extend along parallel axes, and the second rod section 316 is preferably substantially perpendicular to the first rod section 324 and the third rod section 322, although different configurations are within the scope of this invention.

The design of the upper rod 302 enables members of a surgical team to easily rotate or move up or down the entire video projection system, rod assembly, and viewing screen 100. When the system is set up adjacent a surgical table as shown in FIGS. 24 and 25, the second rod section 316 is located generally within a member's grasp. Fingers in a fist grasping the second rod section 316 can either push towards the elbow 318 to rotate the viewing screen 100 in one direction or towards the elbow 320 to rotate the viewing screen in the opposite direction. At the same time, by grasping the second rod section 316, a member can push upwards on the section 316 to move the viewing screen up, or can pull downwards on the section 316 to move the viewing screen down. Movement up and down is accommodated by the support stand 40. Since the relative position between the projector 20 and the viewing screen 100 is not changed by moving the upper rod 302, a member can grasp the section 316 and move the viewing screen freely into preferred viewing locations without fear of ruining the optical image displayed on the viewing screen. Thus, section 316 serves as a "handle" for movement of the viewing screen 100. Alternate embodiments of handles are within the scope of this invention, such as rod or C-shaped devices extending from an upper rod. However, the dog leg design of the upper rod 302 is preferred because section 316 can be accessible to any member of a surgical team regardless of how the rod assembly 300 is positioned. In addition, a single grasp of section 316 allows for movement of the system in any direction.

In addition, the non colinear section of the upper rod 302 creates sufficient friction with a sterile cover 130. The sigmoid shape allows for ready covering of the rod assembly 300 while generating a retention force to retain the cover on the rod assembly. The rod assembly may thus be rendered sterile by cover 130.

Further, as shown in FIG. 25, the non colinear section of the upper rod 302 aligns the upper section with the center of mass of the projector 20 and the lower rod 304 with the optical path. The alignment of the upper section with the center of mass of the projector 20 provides uniform resistance to rotation of the projector with respect to the stand 40.

The lower rod 304 connects the upper rod 302 to a suitable screen mount assembly, which in turn supports the viewing screen 100 adjacent a surgical field for receiving a projected image from the projector 20. The lower rod 304 is pivotally and rotatably movable with respect to the upper rod 302 due to the universal joint assembly 314. Thus, if a patient flinches or wakes up during a surgical procedure or if an emergency or other situation dictates that the viewing screen 100 be removed from the surgical area, the lower rod 304 can easily and quickly be moved out of the way, without having to move the upper rod 302, projector 20 and/or stand. In addition, the precise angular position for the viewing screen to accept the projected image can easily be located by moving the lower rod 304 into position. The projected image may thus be aligned with focused upon the viewing screen 100.

The selected position of the lower rod 304 with respect to the upper rod 302 is retained by friction within the universal joint assembly 314. The friction is sufficient to retain the lower rod 304 and display screen 100 upon operable alignment, while permitting an overriding force to readily move the lower rod. FIG. 23 shows a cross section of the interior of the universal joint assembly 314. The proximal end 310 of the lower rod 304 is inserted and secured within a drilled ball 340. The drilled ball 340, which may be made of stainless steel rests upon a plastic washer 342 which is seated within a ball housing 344. The ball 340 is prohibited from substantial upward movement within the ball housing 344 by a plastic cup 346 which presses down on the ball 340. The friction required for retaining the rod 304 in a selected orientation is thus provided by the combination of the plastic cup 346 above the ball 340 and the plastic washer 342 below the ball 340. Directly above the plastic cup 346 may be a flat disk 348, made preferably of metal and a beleville washer 350. The washer 350 surrounds a portion of a compression screw 352. The compression screw 352 may adjust the compression of the plastic cup 346 on the ball 340, thus setting the degree of force required to move the rod 304 relative to the universal joint assembly 314. The belleville washer 350 serves as a spring for adjusting the compression. Concentric with the ball housing 344 is a ball stop 354 which provides a seat for the distal end 308 of the upper rod 302. The rod 302 is provided with through holes 384 and 386, lying in parallel planes and along perpendicular axes, for alignment with through holes in the ball stop 354 and ball housing 344 for providing a passage for set screws. Through hole 384 is shown in alignment with through hole 382 in ball stop 354 and through hole 380 in ball housing 344. Through hole 380 is preferably countersunk to provide a seat for the head of a set screw. The proximal end 310 of the lower rod 304 is preferably provided with a truncated conical section 311 to prohibit interference between the proximal end 310 and the ball housing 344. Movement of the lower rod 304 relative to the upper rod 302 in a wide variety of positions is thus enabled, with the rod 304 being self-retained in a selected position through the friction mounting.

Upon employment of the universal type joint 314, the operable alignment of the screen 90, 100 and the projector 20 is maintained upon reorientation of the screen adjacent the surgical field 16, or repositioning of the projector 20.

Viewing Screen

The viewing screen material is a styrene of PVC material that has a minimal internal light transmission and scattering. The screen material is rigid and light weight so that only a thin sheet is required to maintain a self supporting planar surface. The display screen has the same dimension as a typical video. The viewing screen 100 is made proportional to the shape of the projected image. In the present embodiment, a horizontal to vertical aspect ratio of 4:3 is used; another common aspect ratio for projected images is 16:9.

As the optical path 12 is substantially vertical in the area of the surgical field 16, the orientation of the viewing screen 90 in a nonhorizontal position provides that the viewing screen is nonperpendicular to the optical path.

In one embodiment, a viewing screen 100 is designed for single use only so as to enhance the sterile environment. Improper cleaning or inadequate sterilization often occurs when end users attempt to reuse prepackaged sterile surgical products. Further, certain sterilization processes can distort the screen thus reducing the image quality of the projected image. In addition, sterilization processes can be expensive and time consuming and can hold up the use of needed materials. Therefore, the present viewing screen 100 is constructed so that if the resterilization or cleaning of the viewing screen attempted the screen will degrade rendering it unusable. In a further embodiment, the viewing screen 100 may incorporate a dye that is activated upon sterilization procedures so that a subsequent user can readily identify that the screen has been used and a sterile screen is required. Because a new viewing screen 100 must be used with each procedure, the integrity of the projected image is guaranteed as well as the sterility of the screen.

Figure 26:
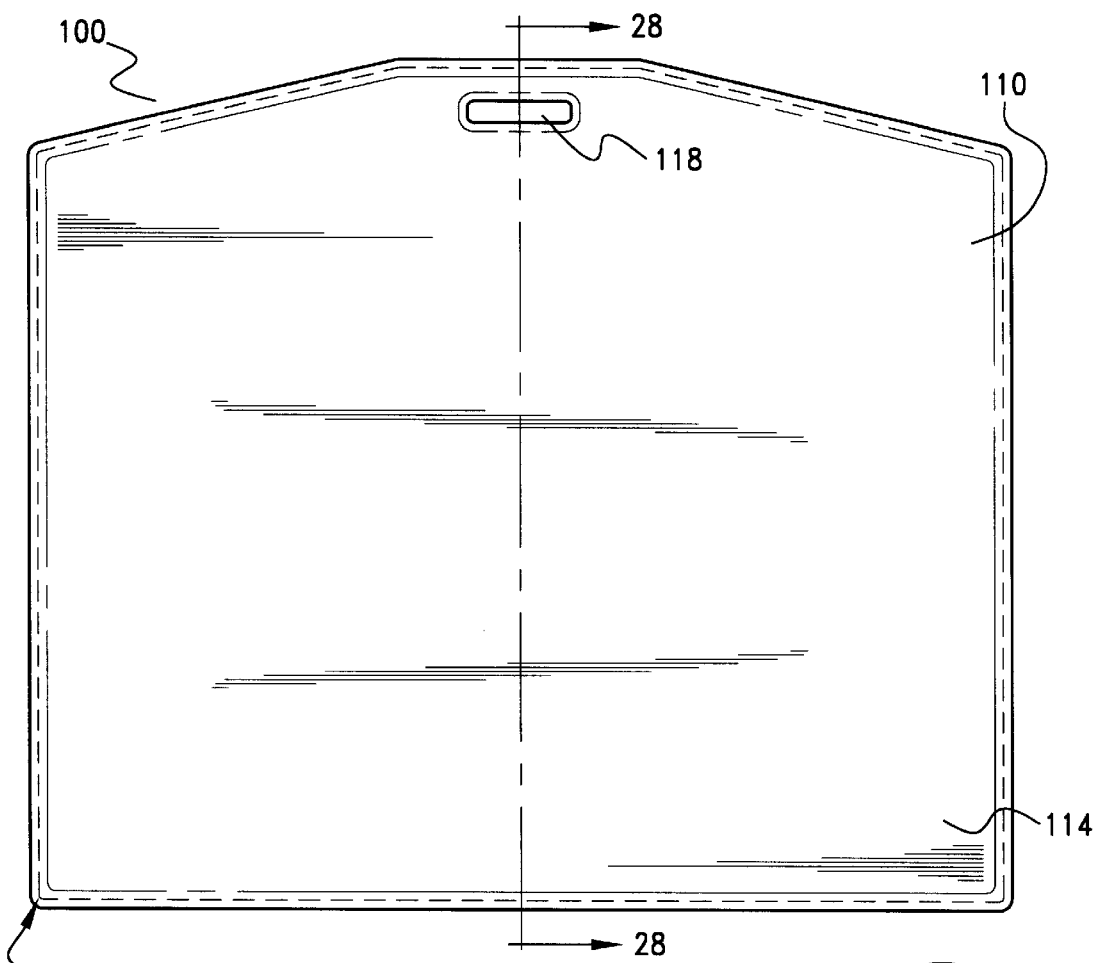
FIG. 26 is a top plan view of a top layer of a viewing screen.

The viewing screen 100 as shown in FIG. 26 is preferably in a pentagon shape for maximum material usage, although other shapes are within the scope of this invention, such as circular or oval. The viewing screen 100 has a top layer 110 which may be made from vacuum formed polystyrene, a reflective material, preferably in white for adequate reflection of the projected image. The material used is preferably between 0.010–0.030 inches thick, and most preferably 0.020 inches thick. The thickness is chosen such that the top layer 110 is thick enough to function in the intended manner without requiring excess material. Therefore he top layer is generally limp and incapable of being self supporting when positioned adjacent a surgical field and yet provides a good image display surface.

Figure 27:
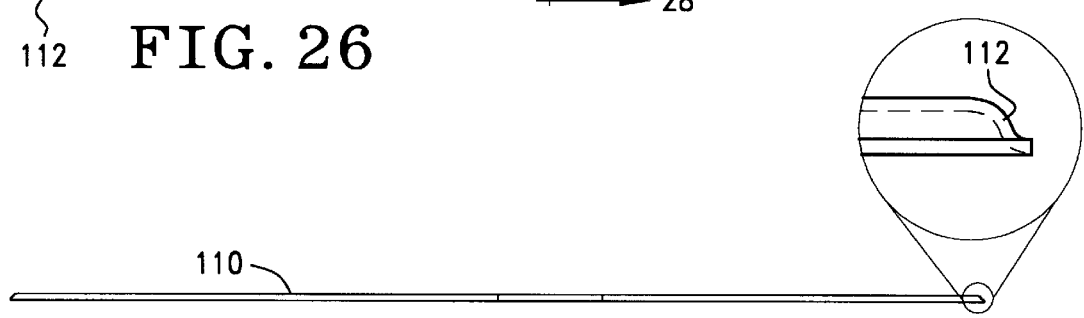
FIG. 27 is a side elevational view of the top layer of the viewing screen of FIG. 26.
Figure 28:
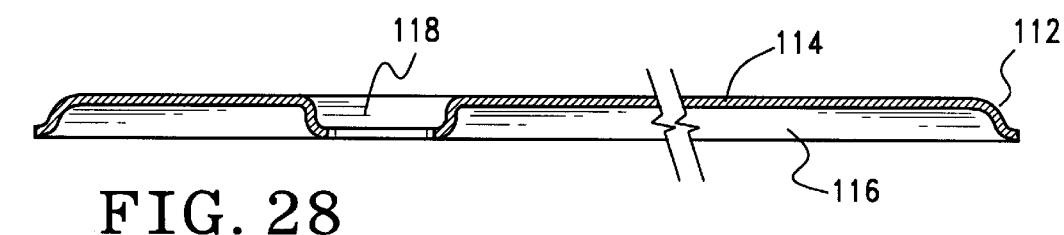
FIG. 28 is a cross-sectional view of the top layer of the viewing screen taken along line 28—28 from FIG. 26.

The top layer 110 is vacuum formed to have curved edges 112, as shown more clearly in FIGS. 27 and 28. The curved edges provide additional structure integrity to the screen 100. The top surface 114 of the top layer 110 between the curved edges 112 is flat and defines the optical surface of the viewing screen 100. The height of the viewing screen 100 from the top surface 114 to the bottom of a curved edge 112 is preferably approximately 0.070 inches. The interior of the top layer 110 defines a recessed space 116 for receiving a rigid backing as will be described. The top layer 110 may further be provided with a slot 118 for mating with a tongue of the screen supporting mechanism, as will be described. If alternative retention systems are chosen supporting the viewing screen, the slot 118 need not be provided.

To provide a 15 inch diagonal viewing screen 100, the top layer 110 may be approximately 9.3 inches high by 12.3 inches wide. An extra 1.0 inch may be provided to the height to accommodate the area for the slot 118. Although these dimensions are currently preferred, alternate dimensions are within the scope of this invention as larger or smaller viewing screens may be desired, or as the distance of the projector to the viewing screen is changed.

Figure 29:
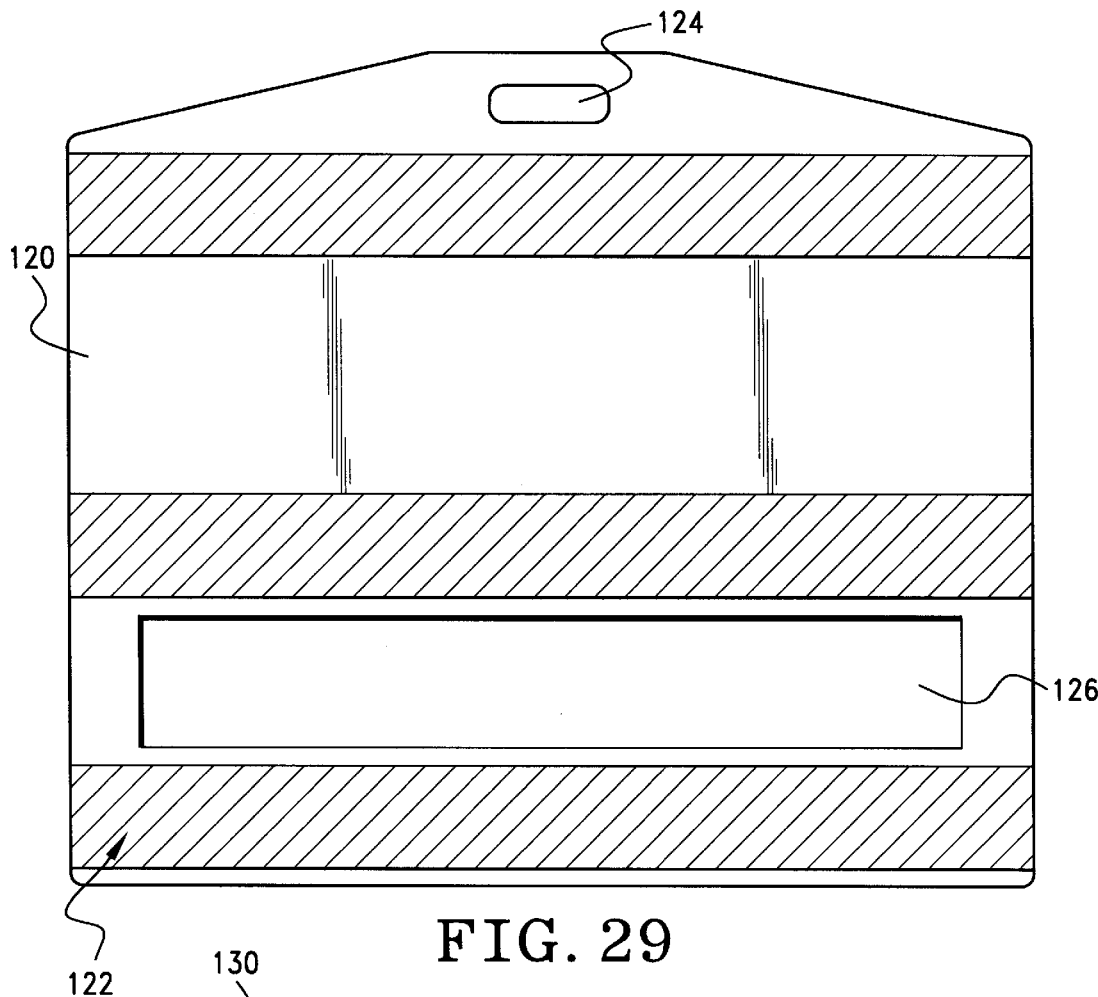
FIG. 29 is a top plan view of a backing for a viewing screen.

Turning now to FIG. 29, a rigid backing 120 is shown for attachment to the rear surface of the top layer 110, within the recessed space 116. Therefore, the rigid backing 120 is preferably substantially the same size as, but slightly smaller than, the top layer 110. That is, for a 15 inch diagonal viewing screen 100, the backing 120 is preferably approximately 9.1 inches high by 12.0 inches wide, with an extra inch at the top to accommodate an area for a slot 124 which is slightly longer and wider than the slot 118 so that the slot 124 can surround the slot 118 when the backing 120 is placed within the top layer 110.

For retaining the backing 120 within the top layer 110, a suitable adhesive may be used. As shown in FIG. 29, strips of double sided adhesive tape, approximately one inch thick, are used. Alternately, an adhesive backing could be used. In any event, the top surface of the backing 120 is adhered to the bottom surface of the top layer 110 to provide rigidity to the top layer 110 for enabling the viewing screen 100 to be self supporting and for enabling the top surface 114 to maintain a flat surface for receiving an image of good optical quality.

Although the viewing screen 100 is described as flat, it should be noted that certain optical systems in a projector may be devised which are designed to project on curved screens. In such a case, it is within the scope of this invention to ensure that the viewing screen 100 is provided with a curvature suited for use with the chosen projection system.

The backing 120 is preferably made from a degradable material, such as cardboard or other paper structure, will degrade when cleaned with water, alcohol, or other fluid. Thus, even if the cardboard or paper structure is put through a resterilization process in which it could survive, it would be impossible to adequately clean the backing after use in the operating room without degrading the material. Alternate materials which cannot withstand any sterilization process are of course within the scope of this invention. In another alternate embodiment, a backing 120 could be made from a material which changes color when put through non-moisture driven sterilization processes to indicate that the viewing screen 100 has been previously used.

A suitable material and thickness for the backing 120 is approximately 0.070 inches of Twinkote paper which is substantially white throughout its thickness. Other paper or plastic materials could also be used. Because the backing 120 is permanently adhered to the top layer 110, if one attempts to clean the screen 100 with fluid or resterilize the viewing screen 100, the cardboard backing 120 will degrade, thus destroying the rigidity necessary for employing the viewing screen 100. It is conceivable that the backing 120, if made from a material having a suitable reflective surface, may be used by itself as a single-use viewing screen; however, because blood and other bodily fluids are not easily wiped from such a degradable backing and may distort the projected image, it is generally preferred to cover the backing 120 with the plastic top layer 110 which can withstand such wiping.

Figure 30:
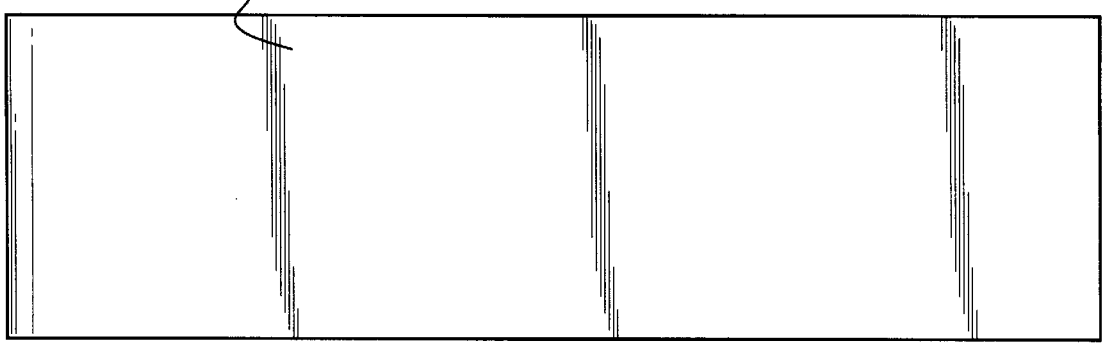
FIG. 30 is a top plan view of a folded screen holder cover.

As further shown in FIG. 29, the backing 120 is provided with a cutout 126. When the backing 120 is adhered to the top layer 110, the cutout 126 and the rear surface of the top layer 110 form a recess for receiving the screen holder cover 130, shown in FIGS. 30 and 31. The cover 130 is a sterile, protective, tubular covering which may be slipped over the screen holder prior to installation of the viewing screen 100. The cover 130 may be made of polyethylene and may be approximately two inches in diameter and 30 inches long, or as wide and long as needed to adequately cover the screen holder. Only one end of the cover 130 need be open. The opposite end may be sealed.

Figure 31:
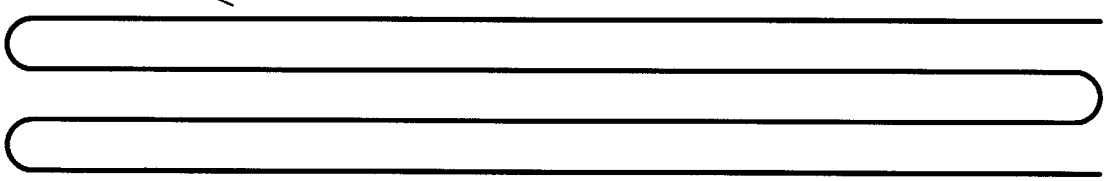
FIG. 31 is a side plan view of the folded screen holder cover from FIG. 30.
Figure 32:
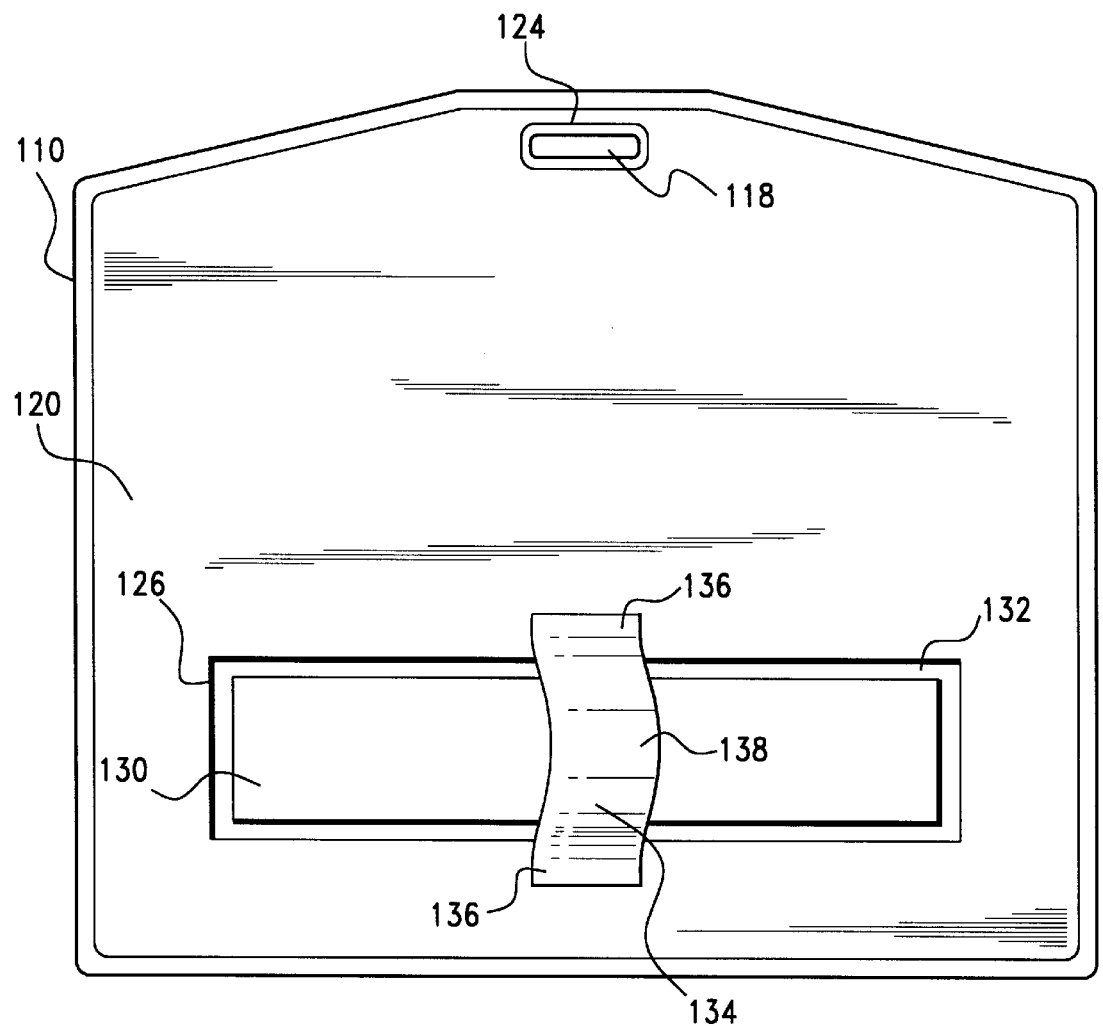
FIG. 32 is a bottom plan view of the top layer, backing, and folded screen holder cover assembled into kit.
Figure 33:
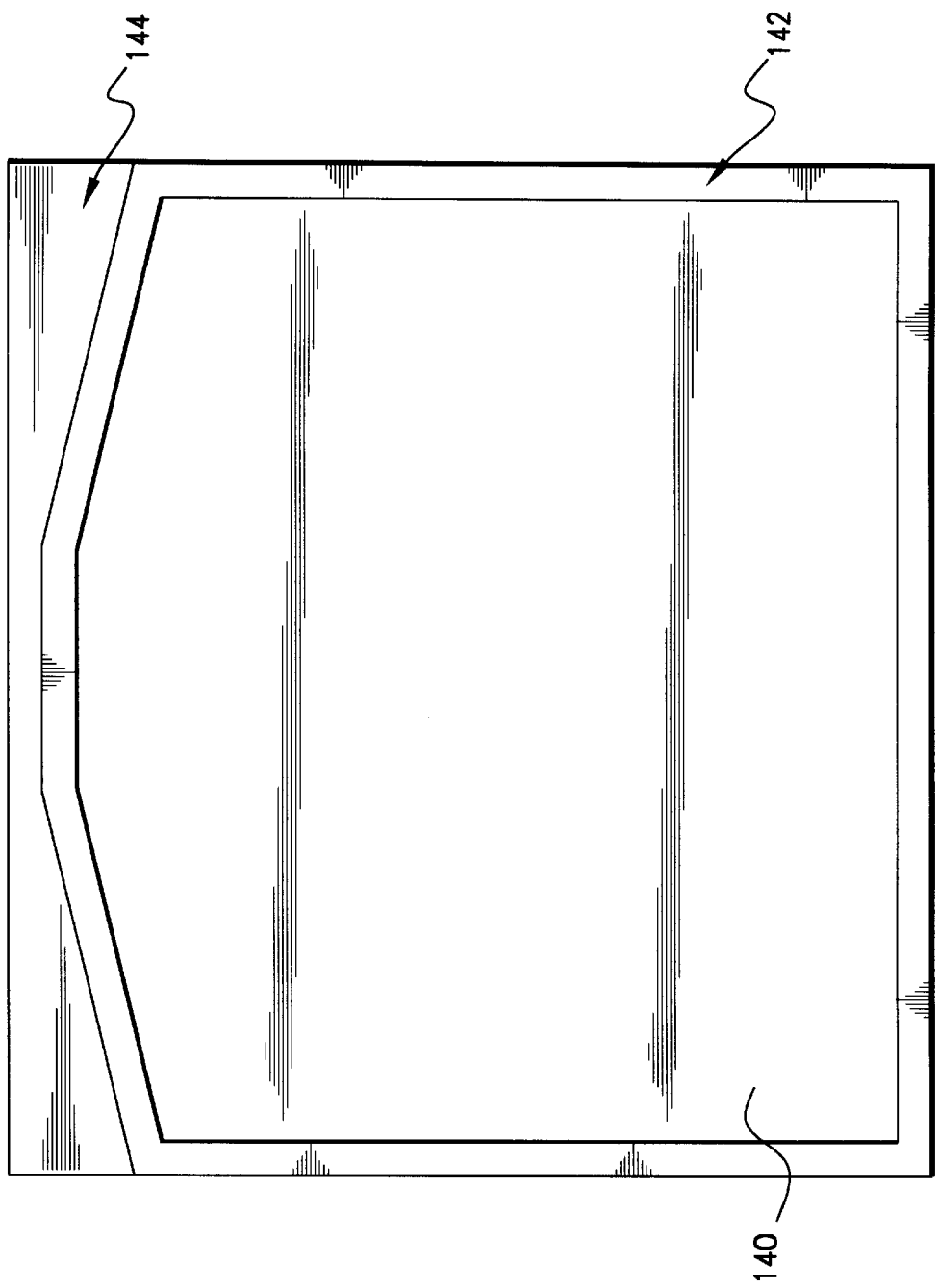
FIG. 33 is a top plan view of a package for the viewing screen assembly of FIG. 32.
Figure 34:
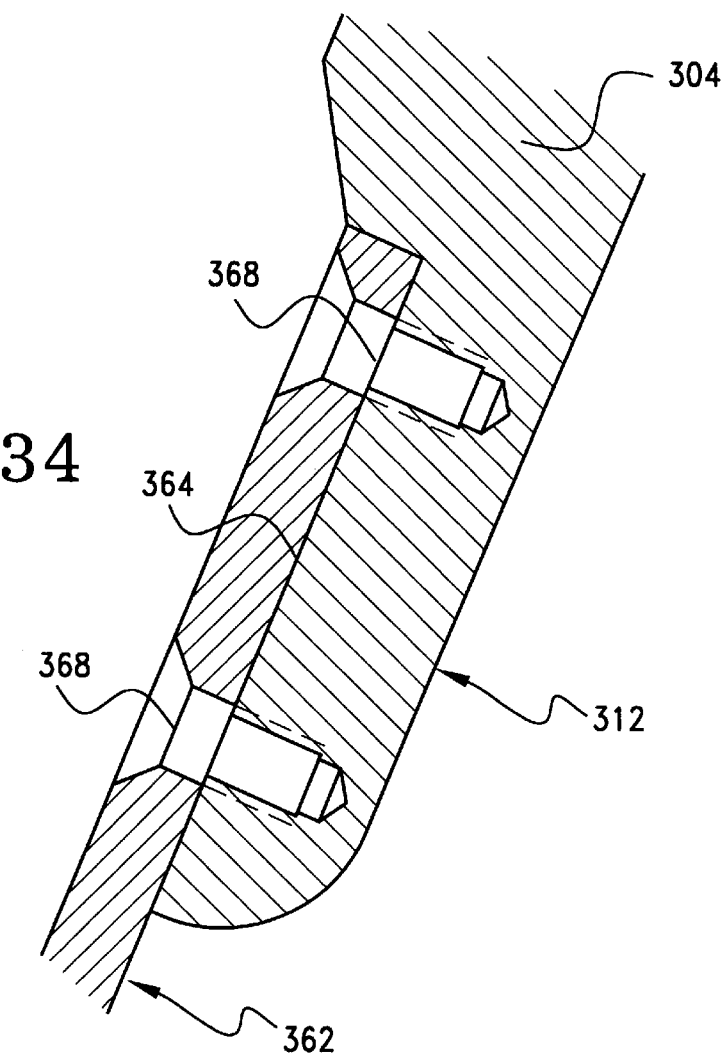
FIG. 34 is a cross-sectional view of the connection between a rod assembly and a screen mount assembly.

The cover 130 is sized to be folded over upon itself, as shown in FIG. 31, and placed within the recess 132 formed by the cutout 126 and the rear surface of the top layer 110, as shown in FIG. 32. The cover 130 may be retained within the recess 132 by a sticker 134 which has adhesive in the areas 136 overlying the backing 120, but which is substantially free of adhesive in the portion 138 overlying the recess 132 so that the cover 130 does not become damaged by removing the cover 130 from the recess 132. If desired, the sticker 134 and/or the backing 120 may include instructional indicia For retaining the viewing screen 100 in a sterile condition, a sterile package 140 as shown in FIG. 33 is preferably provided. The package 140 is preferably sized to be slightly larger than the viewing screen 100 so that the screen is not distorted within the package. The package 140 may be made from two layers of a flexible plastic material, the layers being heat sealed together along edges 142 and provided with a peel apart area 144 for separating the layers and releasing the viewing screen. The package 140 may include instructional indicia either on an insert or on a sticker provided on the outer layer of the package 140.

Although designed for use with the rod assembly and screen mounting system described herein, it should be noted that the inventive viewing screen 90 and degradable viewing screen 100 may be used in other applications in the projection art. Advantageously, the materials used to manufacture the viewing screen 100 are inexpensive, and therefore replacing the degradable viewing screen 100 after each procedure can be safer and more cost-effective than alternatives.

Screen Mounting System

Figure 3A:
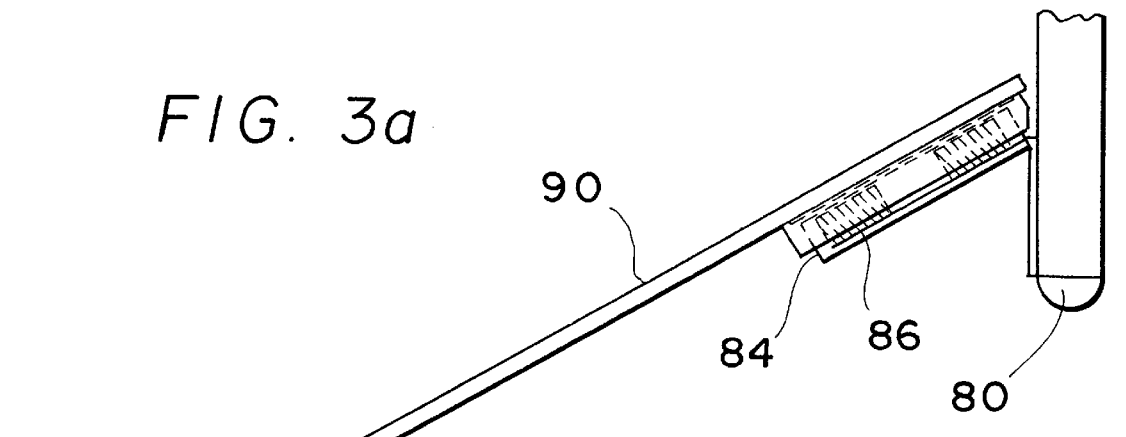
FIGS. 3a and 3b are side elevational views of the first embodiment of attaching the viewing screen to a rod.
Figure 3B:
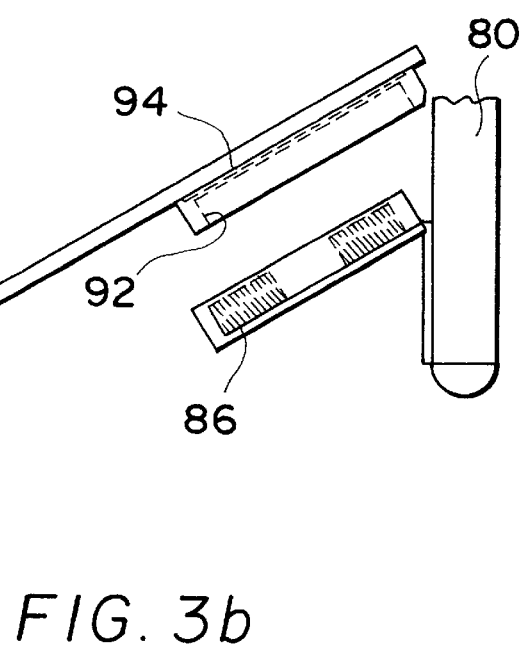

In the first embodiment, as shown in FIGS. 3a and 3b, the screen mount 82 includes a magnetic socket mechanism 84. A plastic encapsulated rectangular magnet 86 is mounted onto the rod 80 and is inclined to the optimal viewing position. The viewing screen 90 includes a socket 92 having a corresponding periphery, wherein the socket includes an embedded layer of steel or other magnetically active material 94. The rectangular shape of the encapsulated magnet 86 matches the shape of the socket 92 so that the screen 90 is easily and accurately placed in the optimal viewing position.

The attraction between the magnet 86 and the steel is sufficient to retain the screen 90 in operable position. However, the magnetic attraction is sufficiently small so that if the patient inadvertently contacts the screen 90, the screen with readily disengage to prevent injury.

Figure 4A:
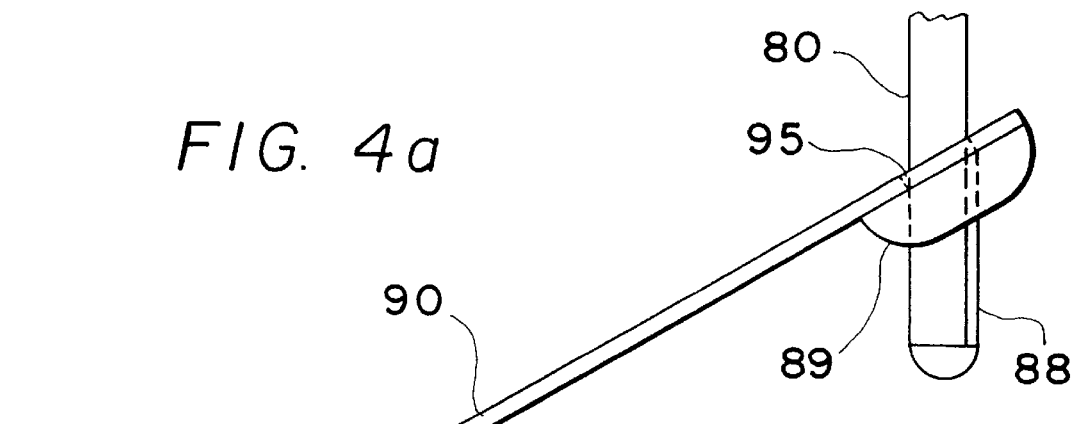
FIGS. 4a and 4b are side elevational views of an alternative attachment of the viewing screen to the mount.
Figure 4B:
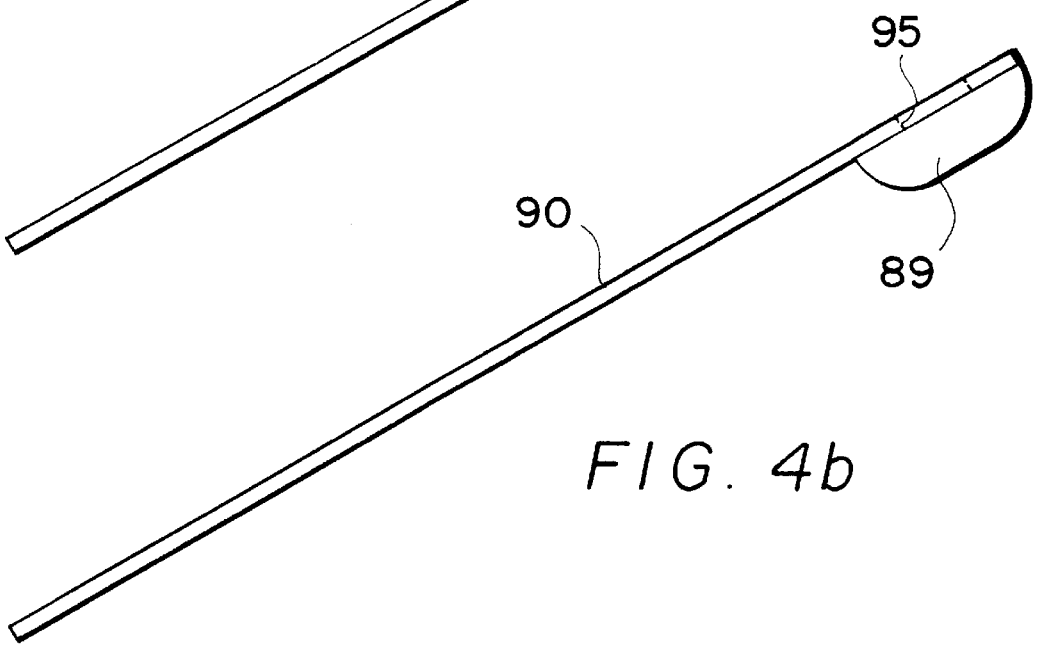

Alternatively, the screen 90 may include spring biased members or a pocket, recess or flange which cooperatively mates with a corresponding structure on the screen mount 82 to releasably and operatively retain the screen relative to the rod 80. In the second preferred embodiment of the screen mount shown in FIGS. 4*a* and 4*b*, the screen 90 includes an aperture 95 and depending stabilizing flanges 89 which mate with a screen mount stop 88 on the rod 80.

A third preferred embodiment of a screen mount shown in FIGS. 21–22 and 34–35 is designed for cooperation with the slots 118 and 124 of the top layer 110 and backing 120, respectively, of the viewing screen 100. The screen mounting assembly 360 includes a generally L-shaped screen holder 362 having a first part 364 angled relative to a second part 366. The first part 364 may be attached to the distal end 312 of the lower rod 304 by screws 368. The distal end 312 is shown including a flat cut-away region for mating with the flat first part 364.

Figure 35:
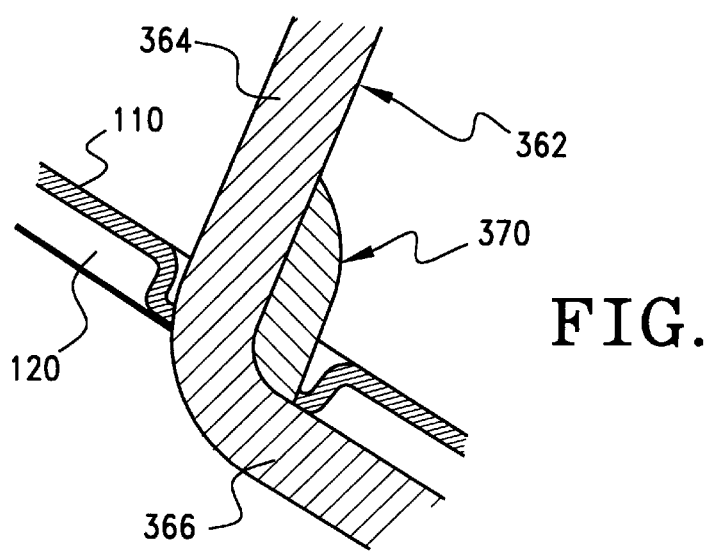
FIG. 35 is a cross-sectional view of a viewing screen mounted on a screen mount assembly.

The second part 366 is a supporting tongue for insertion through the slots 118 and 124 and for supporting the viewing screen 100 adjacent the surgical field. For insertion through the slots, the width of the second part 366 can only be as wide as the slots. Because the viewing screen 100 is rigid, planar, and substantially self-supporting, the second part 366 need not be particularly long. As shown in FIG. 35, the second part 366 lies directly adjacent the backing 120.

The screen mounting assembly 360 further preferably includes features which assist in substantially preventing movement of the viewing screen 100 once it is installed on the assembly 360. First, a screen stop 370 is positioned at the junction of the first part 364 and second part 366. The screen stop 370 may be a generally cylindrical strip of material which fills in the gap which would otherwise be left by the space between the first part 364 and second part 366. The screen stop 370 can alternatively be formed of metal tabs bent up from the tongue 366. By taking up this space, the screen 100 is substantially prevented from drifting to the right or left of the assembly 360. Thus, the screen stop 370 prevents side-to-side wobbling of the screen 100. Further, a pair of shoulders 372, one on each side of the screen holder 362, is provided. The shoulders 372 are formed by providing a first part 364 which is wider than a second part 366. The shoulders 372 can help prevent the viewing screen 100 from being accidentally dislodged when the screen 100 is hit on the top layer 110 or backing 120. The shoulders 372 also prevent up and down wobbling of the screen 100.

In any of the embodiments, it should be noted that the rod assembly and/or the screen mounting assembly may be used to locate a screen display that does not require a projected image. That is, a flat panel type display (e.g. LCD), or other type of display, may also be operably located by the rod assembly and/or screen mounting assembly adjacent a surgical field or other desired location.

Operation

Although the present invention is described in terms of endoscopic and laparoscopic surgery, the invention is applicable to any procedure where it is useful to display information adjacent the viewer and medical, sterile field. The information can be displayed in a video format and include x-rays, ultrasonic or topographic images and vital signs information.

As employed for endoscopic surgery, the location, height and orientation of the viewing screen 90 are preferably set for the surgical team prior to surgery. The articulating arm 48 or adjusting track 52 and counterbalanced arm 56 permit locating the viewing screen 90 horizontally and adjusting the vertical control in arm 48 or arm 56 permits the desired orientation of the viewing screen 90. Preferably, the viewing screen 90 is oriented so that the direction of motion in the projected image on the screen 90 directly corresponds to the direction of motion in the surgical field 16. In addition, the viewing screen 90 is located within arms length (approximately three feet) of the surgical field 16 and below eye level of the viewer. While the viewing screen 90 is optimally located adjacent to and immediately above the surgical field 16, alternative locations are anticipated, wherein the viewing screen may be intermediate or surgical field and eye level of the viewer. In addition, the viewing screen 90 is sufficiently near the surgical field so that a surgeon working in the surgical field which is projected upon the viewing screen 90 can readily point to or touch the viewing screen to identify a portion of the projected image.

Figure 36:
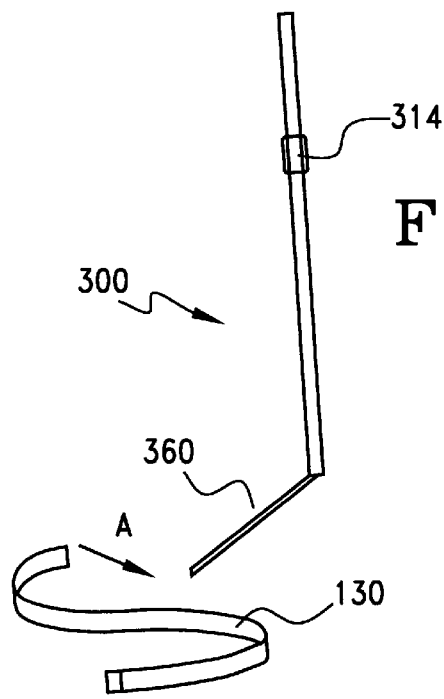
FIG. 36 is a schematic view of a screen holder cover prior to installation on a rod assembly and screen mount assembly.
Figure 37:
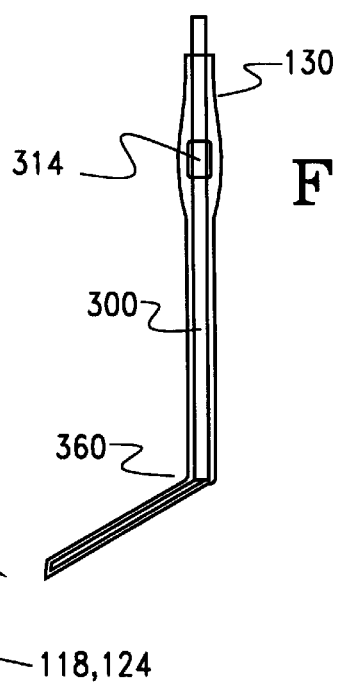
FIG. 37 is a schematic view of a viewing screen prior to installation on a screen mount assembly; and, FIG. 38 is a schematic view of a viewing screen being installed on a screen mount assembly.
Figure 38:
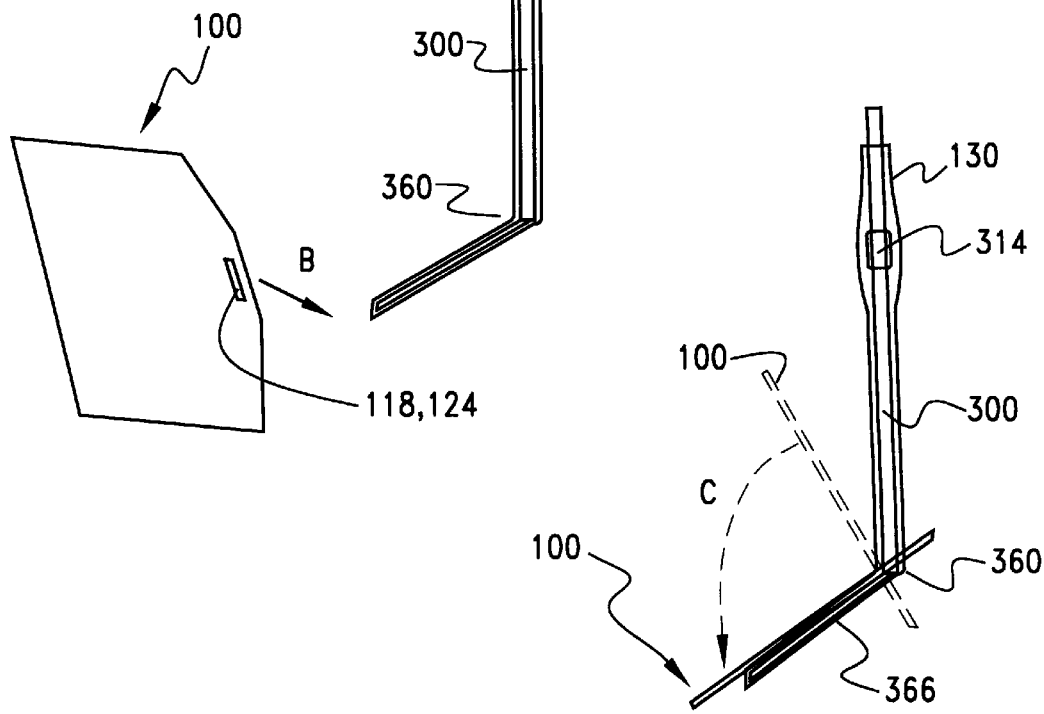

The viewing screen 100 is used in substantially the same manner as the above described method for using the viewing screen 90. To install the viewing screen 100, a circulating nurse should check to see that the sterile package 140 has not been opened or damaged, and should then open the sterile package 140, using a sterile technique, by prying apart the plastic layers of the package 140 at the peel apart area 144. A scrub nurse should then remove the display screen assembly from the package. The screen holder cover 130 should be removed from the recess 132. As shown in FIG. 36, the open end of the screen holder cover 130 should be drawn over the screen mounting assembly in the direction of arrow A. The screen holder cover 130 retains its position on the rod assembly 300 by gathers in the cover 130 and due to the protrusions and bends on the rod assembly 300. As shown in FIG. 37, after the screen holder cover 130 is properly installed, the viewing screen 100 may be mounted onto the screen mounting assembly 360. With the top layer 110 facing the screen mounting assembly 360, the slots 118, 124 of the viewing screen 100 are placed onto the second part 366 of the mounting assembly 360, in the direction of arrow B. The viewing screen 100 is pushed over the second part 366 until the slots line up with the junction of the first part 364 and second part 366 of the screen holder 362, as shown in phantom in FIG. 38. The viewing screen 100 may then be released or placed such that the viewing screen 100 moves in the direction of arrow C to rest on the second part 366. During an operative procedure, the top layer 110 of the viewing screen 100 may be wiped with a dry cloth or with a cloth dampened with sterile water or alcohol. Following a procedure, the viewing screen 100 and the screen holder cover 130 should be removed and discarded.

An active video signal and standard AC electrical power inputs are connected to the video projector 20 from the gathering system 8 and converter 4. The active video signal may come from the endoscope or another image generating mechanism trained on a portion of the surgical field 16. The video projector 20 transfers the electrical video signal into an optical image and projects the optical image along the optical path 12. The image size and focus are set by the details of the system so that they match the viewing screen size and location.

The present invention is directed to a viewing screen which may be appropriately positioned and angled within a sterile, surgical field to provide convenience and image quality necessary for successful surgical procedures.

The unique restrictive conditions found in a surgical setting require that a viewing or display system satisfy the conditions that:

1. Neither the surgeon, the surgical instruments nor the surrounding operating room equipment should interfere with or compromise the function of the display system;
2. Complex electronics and unnecessary hardware should not be introduced into the sterile surgical environment;
3. The size and weight of anything introduced into the surgical field should be no greater than as required by the useful function; and
4. Blood and other surgical fluids must not seriously impair the function of the display system.

The present use of a video projector physically separates the viewing screen (projected image) from the illumination hardware, illumination electronics, video processing electronics, the display power electronics, the image transmission line (connected to the image gathering system) and the display power cable. Further, the use of video projector technology allows the image to be viewed on a light weight screen that may be formed of materials resistant to blood and surgical fluids. To additionally achieve: (1) the required clarity in the displayed image, (2) a viewing screen convenient to the surgeons, and (3) flexibility in the projector's mounting configuration and orientation with respect to the surgical field, it has been found by the present inventors that this requires the depth of focus and the tilt of the focal plane of the projected image relative to the optical axis to be appropriately manipulated. The manipulation of the depth of field and the angle of the focal plane with respect to the optical axis is done so that the projected image displayed on the viewing screen has a substantially uniform focus across the screen and its resolution is not limited by defocusing, while image brightness is maximized.

The concept of depth of focus rests on the assumption that for a given optical system, there exists a blur (due to defocusing) of small enough size such that it will not adversely affect the usefulness of the system. The depth of focus is the amount by which the image may be shifted longitudinally with respect to some reference plane and introduce no more than the acceptable blur. That is, the depth of focus is defined by the amount by which any point in the image (any point on the viewing screen) may be shifted along the optical axis with respect to the video projector and will deliver an image that is substantially free from unacceptable defocusing blur. The video projector depth of focus is based on the concept that a defocused blur which is smaller than a pixel in the image is not substantially noticeable. The image pixels are determined by the image generating device in the video projector (for example the LCD panels in an LCD video projector).

There is a volume of space, the focal volume, defined by the size of the projected image at the focal plane and by the video projector depth of focus on either side of the focal plane. The focal plane is a plane of "best" focus for the system. Within the focal volume, sufficient image clarity (defocus blur smaller than pixel size) and a convenient viewing screen angle can both be achieved.

At one extreme, the focal volume is relatively small and substantially planar, or plate like. When the focal volume is plate like and the viewing screen relative to the optical axis is substantial, for example 30 degrees, the focal plane must be tilted relative to the optical axis in such a way that the focal plane is substantially parallel to and in the same location as the tilted viewing screen. Thus, the viewing screen surface falls completely within the focal volume. A plate like focal plane that is tilted relative to the optical axis is realized by disposing a projection lens, having a relatively large clear aperture, in the optical path so that the projected image passes through the projection lens and so that the projection lens has an optical axis tilted with respect to the optical path. This provides for a relatively bright and focused image across the viewing screen.

In another extreme, the focal volume is large and slab like. The focal volume is thick enough (extends sufficiently along the optical path) that the viewing screen may be disposed entirely within the focal volume even if the focal plane and the viewing screen surface are not substantially parallel to each other. A slab like focal plane is realized by disposing a projection lens, having a relatively small clear aperture, in the optical path so that the projected image passes through the projection lens. If there are no tilting projection optics employed, then the normal to the focal plane is parallel to the optical axis, yet, the normal to the viewing screen may be disposed approximately 30 degrees from the optical axis while maintaining a projected image clarity of acceptable defocused blur.

Between these two extreme configurations, a combination of many factors will dictate the desired compromise of the focal plane tilt and depth of focus. These factors include video projector mounting configuration, screen angle, image size, image resolution (number of pixels), distance between the screen and the projector, optical aberrations, the size and numerical aperture of the projector's image generating device and the desired or required projected image brightness.

While preferred embodiments of the invention have been shown and described with particularity, it will be appreciated that various changes and modifications may suggest themselves to one having ordinary skill in the art upon being apprised of the present invention. It is intended to encompass all such changes and modifications as fall within the scope and spirit of the appended claims.

What is claimed is:

1. A display system for medical imaging, the display system comprising:
   (a) a sterile front projection screen for viewing a projected image;
   (b) an indicator for indicating an attempted resterilization of the projection screen; and
   (c) a sterile package encompassing the sterile front projection screen and the indicator.

2. The display system of claim 1 wherein the sterile screen comprises a degradable layer of self-supporting materal.

3. The display system of claim 2 wherein the sterile screen comprises a reflective layer bonded to the degradable layer and having the reflective surface, the reflective layer being non self-supporting without the degradable layer.

4. The display system of claim 3 wherein the reflective layer is made from a vacuum formed plastic sheet having a recessed space for receiving a portion of the degradable layer.

5. The display system of claim 4 wherein the degradable layer is provided with a cut-out, the cut-out and a rear surface of the reflective layer defining a recessed pocket adapted for receiving a folded sleeve cover.

6. A display system for a medical imaging system, the display system comprising:
   (a) a sterile front projection screen; and
   (b) a dye activated upon resterilization to change from a first color to a second color.

7. A medical imaging display system, comprising:
   (a) a sterile front projection screen of a first color for viewing a projected image, the screen including a material having a second resterilization activated color upon resterilization.

8. A display system for a medical imaging system, comprising:
   (a) a sterile front projection screen; and
   (b) a resterilization indicator sufficiently connected to the sterile front projection screen to substantially preclude non-destructive separation from the sterile projection screen.

9. A display assembly, comprising:
   (a) a sterile front projection screen;
   (b) an indicator having a first configuration before an attempted resterilization of the screen and a second configuration after the attempted resterilization of the screen; and
   (c) a sterile package encompassing the sterile front projection screen and the indicator.

10. The display system of claim 9, wherein the first configuration of the indicator is a first color and the second configuration of the indicator is a different second color.

11. The display system of claim 9, wherein the first configuration of the indicator defines first surface profile and the second configuration of the indicator defines a different second surface profile.

12. The display system of claim 9, wherein the first configuration of the indicator creates a first representation of a projection image and the second configuration of the indicator creates a different second representation of the projection image.

13. A display system for a medical imaging system, comprising:
   (a) a sterile single-use front projection screen formed of a material having minimal internal light transmission and scattering so as to provide a reflective surface capable of reflecting an image of a surgical site projected onto the screen, the screen having a first sterile configuration and a second different configuration in response to an attempted resterilization; and
   (b) a sterile package encompassing the sterile front projection screen.

14. A display system for a medical imaging system, comprising:
   (a) a sterile single-use front projection screen, the screen being formed of a material having minimal internal light transmission and scattering so as to provide a reflective surface capable of reflecting an image of a surgical site projected onto the screen and he screen being degradable upon an attempted resterilization; and
   (b) a sterile package encompassing the sterile projection screen.

* * * * *